US007731965B2

(12) United States Patent
Shih et al.

(10) Patent No.: US 7,731,965 B2
(45) Date of Patent: Jun. 8, 2010

(54) HUMAN RING SPECIFIC BNP ANTIBODIES

(76) Inventors: Jessie W. Shih, 1415 Edgewood Rd., Lake Forest, IL (US) 60045; Joan D. Tyner, 37835 N. Orchard Rd., Beach Park, IL (US) 60087; Matthew S. Matias, 2100 Cranbrook Rd., Green Oaks, IL (US) 60048; Mary S. Pinkus, 5948 N. Landers, Chicago, IL (US) 60646; Susan E. Brophy, 2477 Mallard Dr., Lindenhurst, IL (US) 60046; David J. Dagfal, 7203 97$^{th}$ Ave., Kenosha, WI (US) 53142; David J. Hawksworth, 2643 N. Cherry Cove La., Round Lake Beach, IL (US) 60073; Bryan C. Tieman, 140 S. Rex Blvd., Elmhurst, IL (US) 60126

( * ) Notice: Subject to any disclaimer, the term of this patent is extended or adjusted under 35 U.S.C. 154(b) by 0 days.

(21) Appl. No.: 11/135,040

(22) Filed: May 23, 2005

(65) Prior Publication Data

US 2006/0183154 A1    Aug. 17, 2006

Related U.S. Application Data

(60) Provisional application No. 60/653,829, filed on Feb. 17, 2005.

(51) Int. Cl.
*A61K 39/395* (2006.01)
*A61K 39/00* (2006.01)
*C12P 21/08* (2006.01)

(52) U.S. Cl. ............. 424/141.1; 424/141.2; 424/130.1; 435/70.21; 530/388.1

(58) Field of Classification Search ........................ None
See application file for complete search history.

(56) References Cited

U.S. PATENT DOCUMENTS

| | | |
|---|---|---|
| 4,399,216 A | 8/1983 | Axel et al. |
| 4,510,245 A | 4/1985 | Cousens et al. |
| 4,607,023 A | 8/1986 | Thibault et al. |
| 4,634,665 A | 1/1987 | Axel et al. |
| 4,816,567 A | 3/1989 | Cabilly et al. |
| 4,968,615 A | 11/1990 | Koszinowski et al. |
| 5,114,923 A | 5/1992 | Seilhamer et al. |
| 5,168,062 A | 12/1992 | Stinski |
| 5,179,017 A | 1/1993 | Axel et al. |
| 5,468,646 A | 11/1995 | Mattingly et al. |
| 5,545,806 A | 8/1996 | Lonberg et al. |
| 5,674,710 A | 10/1997 | Seilhamer et al. |
| 6,090,382 A | 7/2000 | Salfeld et al. |
| 6,117,644 A | 9/2000 | DeBold |
| 6,124,430 A | 9/2000 | Mischak et al. |
| 6,162,902 A | 12/2000 | Mischak et al. |
| 6,376,207 B1 | 4/2002 | Mischak et al. |
| 6,461,828 B1 | 10/2002 | Stanton et al. |
| 6,677,124 B2 | 1/2004 | Tsuji et al. |
| 7,341,838 B2 | 3/2008 | Buechler et al. |
| 7,351,586 B2 | 4/2008 | Friese et al. |
| 2003/0022235 A1 | 1/2003 | Dahlen et al. |
| 2003/0162710 A1 | 8/2003 | Sudoh et al. |
| 2003/0199000 A1 | 10/2003 | Valkirs et al. |
| 2004/0132013 A1 | 7/2004 | DeBold |
| 2004/0175379 A1 | 9/2004 | DeVries et al. |
| 2004/0180396 A1 | 9/2004 | Bergmann et al. |
| 2004/0209307 A1 | 10/2004 | Valkirs et al. |
| 2004/0219509 A1 | 11/2004 | Valkirs et al. |
| 2004/0243010 A1 | 12/2004 | Zoghbi et al. |
| 2004/0253655 A1 | 12/2004 | Tsuji et al. |
| 2005/0014287 A1 | 1/2005 | Friese et al. |
| 2005/0064511 A1 | 3/2005 | Buechler et al. |
| 2006/0121042 A1 | 6/2006 | Dall' Acqua et al. |
| 2006/0183154 A1 | 8/2006 | Shih et al. |

FOREIGN PATENT DOCUMENTS

| | | |
|---|---|---|
| EP | 0418308 | 8/1995 |
| EP | 384176 | 12/1995 |
| EP | 5 422 55 | 2/1999 |
| EP | 914344 | 6/2005 |
| EP | 1030177 | 6/2005 |
| EP | 1 016 867 | 1/2006 |
| JP | 3-297392 | 12/1991 |
| JP | 2676114 | 11/1997 |
| WO | 2004/094460 | 11/2004 |

OTHER PUBLICATIONS

Benjamini et al. Immunology, a short course. 2nd edition, Wiley-Liss. 1991, p. 40.*
von Mehren et al. Curr. Opin. Oncol. 1996. 8: 493-8.*
Bogan, et al., J. Mol. Biol. 280, 1-9,(1998).
Cataliotti, et al., Mayo Clin. Proc. 76, 1111-1119, (2001).
Davidson, et al., Journal of Hypertension 12(4), 329-336, (1994).
Galfre, et al., Nature 266, 550-552 (1977).
Ma, et al., PNAS 100(10), 5772-5777, (2003).
Morrison, et al., Proc. Natl. Acad. Sci. USA, 81, 6851-6855 (1984).
Motwani, Lancet 341, 1109-1113 (1993).
Mukoyama, et al., J. Clin. Invest. 87, 1402-1412 (1991).
Shimizu, et al, Clinica chimica Acta 316, 129-135 (2002).
Thorpe, et al., Scandinavian Journal of Immunology 57, 85-92 (2003).

(Continued)

*Primary Examiner*—Christine J Saoud
*Assistant Examiner*—Chang-Yu Wang
(74) *Attorney, Agent, or Firm*—Audrey L. Bartnicki

(57) ABSTRACT

The present invention relates to antibodies that specifically bind to human BNP and immunoassays using said antibodies in the quantification of human BNP or a fragment of human BNP in a test sample.

2 Claims, 8 Drawing Sheets

OTHER PUBLICATIONS

Valli, et al., J. Lab. Clin. Med. 134(5), 437-444 (1999).
Yandle, et al., Journal of Internal Medicine 235, 561-576, (1994).
Yoshibayashi, et al. New Eng. J. Med. 327, 434-434 (1993).
Apple, F.S., et al., "Quality Specifications for B-Type Natruiuretic Peptide Assays", Clin. Chem., 51(3):486-493 (2005).
Axsym BNP package insert, Abbott Diagnostic Division, Feb. 2004.
Belenky, A., et al., "The effect of class-specific protease inhibitors on the stabilization of B-type natriuretic peptide in human plasma", Clinica Chimica Acta, 340:163-172 (2004).
Berzofsky, J.A., et al., "Antigen-Antibody interactions and Monoclonal Antibodies", Fund. Immunol., 2:315-336 (1998).
Bird, R.E., et al., "Single-Chain Antigen-Binding Proteins", Science, 242:423-426 (1988).
Bluestein, B., "Comparing BNP Assays", Bayer Healthcare Diagnostic Div. Publ., (2004).
Boder, E.T. 7 Wittrup, K.D., "Optimal Screening of Surface-Displayed Polypeptide Libraries", Biotechnol. Prog., 14:55-62 (1998).
Boder, E.T. & Wittrup, K.D., "Yeast Surface Display for Directed Evolution of Protein Expression, Affinity, and Stability", Meth. in Enzymol., 10:430-444 (1999).
Boder, E.T. & Wittrup, K.D., "Yeast surface display for screening combinatorial polypeptide libraries", Nature Biotech., 15:553-557 (1997).
Boder, E.T., et al., "Directed evolution of antibody fragments with monovalent femtomolar antigen-binding affinity", PNAS, 97(20):10701-10705 (2000).
Boss, M.A. & Wood, C.R., "Genetically engineered antibodies", Immunol. Today 6(1):12-13 (1985).
Brandt, I., et al., "Dipeptidyl-Peptidase IV Converts Intact B-Type Natriuretic Peptide into Its des-SerPro Form", Clinical Chem., 52(1):82-87 (2006).
Brown, T., "Hybridization Analysis of DNA Blots", Curr. Protocols in Molec. Biol., 2.10.1-2.10.3 (1997).
Buckley, M.G., "Cardiac peptide stability, aprotinin and room temperature: importance for assessing cardiac function in clinical practice", Clin. Sci., 97:689-695 (1999).
Diagnostic Automation/Cortez Diagnostics, Inc., "Nt-proBNP ELISA Quantitative Determination of Nt-proBNP in Biological Fluids", (Cat. No. 2852-7), pp. 1-8 (1997).
Gutkowska, J., et al., "Atrial Natriuretic Factor in Human Plasma", Biochem. & Biophys. Res. Comm., 139 (1):287-295 (1986).
Holmes, S.J., et al., "Renal, Endocrine, and Hemodynamic Effects of Human Brain Natriuretic Peptide in Normal Man", J. of Clin. Endocrinol. & Metab., 76(1):91-96 (1993).
Huston, J.S., et al., "Protein engineering of antibody binding sites: Recovery of specific activity in a anti-digoxin single-chain Fv analogue produced in *Escherichia coli*", PNAS, 85:5879-05883 (1988).
Itoh, H., et al., "Preparation of Monoclonal Antibodies against Brain Natriuretic Peptide and Their Application to Radioimmunoassay and Passive Immunization", Endocrinology, 127(3):1292-1330 (1990).

Kabat, et al., U S Dept. of Health & Human Serv., NIH Publ 91-3242, 5th Ed., Tbl. of Cont.
Kaufman, R.J. & Sharp, P.A., "Amplification and Expression of Sequences Cotransfected with a Modular Dihydrofolate Reductase Complementary DNA Gene", J. Mol. Biol., 159:601-621 (1982).
Kenny, A.J., et al., "Hydrolysis of human and pig brain natiruretic peptides, urodilatin, C-type natriuretic peptide and some C-receptor ligands by endopeptidase-24.11", Biochem. J., 291:83-88 (1993).
Mizushima, S. & Nagata, S., "pEF-BOS, a powerful mammalian expression vector", Nucl. Acids Res., 18(17):5322 (1990).
Murdoch, D.R., et al., "Brain natriuretic peptide is stable in whole blood and can be measured using a simple rapid assay: implications for clinical practice", Heart, 78:594-597 (1997).
Nordin, H., et al., "Kinetic studies of small molecule interactions with protein kinases using biosensor technology", Analyt. Biochem., 340:359-368 (2005).
Rajpal, A., et al., "A general method for greatly improving the affinity of antibodies by using combinatorial libraries", PNAS, 102(24):8466-8471 (2005).
Sanz, M.P., et al., "Comparison of BNP and NT-proBNP Assays in the Approach to the Emergency Diagnosis of Acute Dyspnea", J. of Clin. Lab. Analy., 20:227-232 (2006).
Schiestl, R.H. & Gietz, R.D., "High efficiency transformation of intact yeast cells using single stranded nucleic acids as a carrier", Curr. Genet., 16:339-346 (1989).
Shimizu, H., et al., "Degradation of human brain natriuretic peptide (BNP) by contact activation of blood coagulation system", Clinica Chimica Acta, 305:181-186 (2001).
Strauss, W.M., "Hybridization with Radioactive Probes", Curr. Protocols in Molec. Biol., 6.3.1-6.3.6 (1997).
Tetin, S.Y., et al., "Interactions of Two Monoclonal Antibodies with BNP: High Resolution Epitope Mapping Using Fluorescence Correlation Spectroscopy", Biochem., 45:14155-14165 (2006).
Urlaub, G. & Chasin, L.A., "Isolation of Chinese hamster cell mutants deficient in dihydrofolate reductase activity", PNAS, 77(7):4216-4220 (1980).
Walther, T., et al., "Biochemical analysis of neutral endopeptidasse activity reveals independent catabolism of atrial and brain natriuretic peptide", Biol. Chem., 385:179-184 (2004).
Watanabe, J., et al., "Prognostic Value of Plasma Brain Natriuretic Peptide Combined With left Ventricular Dimensions in Predicting Sudden Death of Patients With Chronic Heart Failure", J. of Cardian Failure, 11(1):50-55 (2005).
Zahnd, C., et al., "Directed in Vitro Evolution and Crystallographic Analysis of a Peptide-binding Single Chain Antibody Fragment (scFv) with Low Picomolar Affinity", J. of Biol. Chem., 279(18):18870-18877 (2004).
McCafferty, J., et al., "Phage antibodies: filamentous phage displaying antibody variable domains", Nature, 348:552-554 (1990).

\* cited by examiner

HUMAN RING SPECIFIC BNP ANTIBODIES

RELATED APPLICATION INFORMATION

This application claims priority from U.S. Provisional Patent Application Ser. No. 60/653,829, filed Feb. 17, 2005.

FIELD OF THE INVENTION

The present invention relates to antibodies that recognize unique epitopes of human BNP, methods for producing said antibodies and immunoassays for human BNP that employ said antibodies.

BACKGROUND OF THE INVENTION

Atrial natriuretic peptide (hereinafter referred to as "ANP"), brain natriuretic peptide (hereinafter referred to as "BNP"), C-type natriuretic peptide (hereinafter referred to as "CNP") and Dendroaspis natriuretic peptide (hereinafter referred to as "DNP") are each members of a family of hormones known as "natriuretic peptides". ANP and BNP share a wide spectrum of biological properties and belong to the cardiac natriuretic system. Both ANP and BNP are of myocardial cell origin while CNP is of endothelial cell origin. DNP was isolated from the venom of the green mamba snake and possesses structural similarity to ANP, BNP and CNP.

BNP received its name because it was first isolated from porcine brain, thus "BNP" stood for "brain natriuretic peptide". However, because BNP belongs to the cardiac natriuretic system, "brain" has been changed to "B-type". Therefore, "BNP" now refers to "B-type natriuretic peptide".

ANP is secreted by the heart in the atria. BNP is secreted by the heart through the coronary sinus, predominantly from the cardiac ventricles. BNP is secreted as a 108 amino acid polypeptide precursor (See Valli et al., *J. Lab. Clin. Med.*, 134(5):437-444 (November 1999)). The mature form of BNP is made up of 32 amino acids (representing amino acids 77-108 of the 108 amino acid polypeptide precursor) with a 17 amino acid ring closed by a disulfide bond between two cysteine residues, an amino-terminal tail of 9 amino acids, and a carboxyl-terminal tail of 6 amino acids. ANP and CNP also have a 17 amino acid ring closed by a disulfide bond between two cysteine residues. Eleven of the seventeen amino acids in the ring are conserved between the three molecules. In addition to the 17 amino acid ring structure, ANP has an amino-terminal tail of 6 amino acids and a carboxy-terminal tail of 5 amino acids. ANP is produced as a 126 amino acid pro-ANP form that is the major storage form of ANP. After proteolytic cleavage between amino acids 98 and 99, the mature 28 amino acid peptide ANP is found in coronary sinus plasma (See Yandle, *J. Internal Med.*, 235:561-576 (1994)).

CNP is found in the brain and cerebral spinal fluid and is the most prevalent of the three peptides in the central nervous system. Little if any CNP is present in the heart. Pro-CNP is a 103 amino acid peptide that is processed into either CNP-53 (amino acids 51 to 103) or CNP-22 (amino acids 82 to 103) that are the active peptides. In addition the 17 amino acid ring structure, CNP-22 has an amino-terminal tail of 5 amino acids and contains no carboxy-terminal tail. CNP-53 is identical to CNP-22 except for a 31 amino acid extension at the amino terminal end.

As mentioned previously, DNP was isolated from the venom of the green mamba snake. The mature form of DNP is made up of 38 amino acids. DNP-like immunoreactivity (DNP-LI) has been reported in human plasma and the plasma concentration of DNP-LI has been found to be elevated in patients with congestive heart failure (See, Cataliotti, et al., *Mayo Clin. Proc.*, 76:111-1119 (2001)). Additionally, it is also known that the infusion of synthetic DNP results in marked natriuresis and diuresis in association with increased plasma and urinary cyclic guanosine monophosphate. Id.

One of the problems with natural human natriuretic peptides is that they are unstable in plasma and serum. Specifically, enzymes, such as proteases, cleave these peptides. For example, proteases cleave BNP (natural and synthetic) at various locations along its amino acid chain. For example, protease cleavage is known to occur at the amino terminus of BNP between amino acids 2-3 (Shimizu et al., *Clinica Chimica Acta*, 316:129-135 (2002)) and at its carboxy terminus between amino acids 30-32. Moreover, endopeptidase cleavage of BNP is also known in the art (Davidson and Struthers, *J. Hypertension*, 12:329-336 (1994)).

The measurement of mature BNP (i.e., the 32 amino acid molecule (amino acids 77-108 of the precursor polypeptide of BNP)) in humans (hereinafter referred to has "Hbnp"), in the general population has been found to reflect cardiac diseases, such as congestive heart failure, ischemic heart diseases, atrial fibrillation and renal dysfunction. In fact, elevated levels of BNP in human plasma has been reported in heart disease, following acute myocardial infarction and during symptomless or subclinical ventricular dysfunction (See Mukoyama et al., *J. Clin. Invest.*, 87:11402-11412 (1991), Motwani et al., *Lancet*, 341:1109-1113 (1993), Yoshibayashi et al., *New Eng. J. Med.*, 327:434 (1992)). Increased circulating levels of ANP are seen in congestive heart failure, chronic renal failure and in severe hypertension. The presence of CNP in human plasma remains controversial with reports of its absence or presence as CNP-22 (See Yandle, *J. Internal Med.*, 235:561-576 (1994)).

A ligand binding assay is an analytical technique for measuring concentrations of substances commonly referred to as ligands that react selectively with specific binding proteins. Immunoassays that measure the concentrations of antigens that react selectively with specific antibodies are an example of a class of ligand binding assays.

Ligand binding assays, such as immunoassays, for measuring human natriuretic peptides in plasma, particularly Hbnp, are well-known in the art and are commercially available. These immunoassays require the use of at least one or two specific antibodies as well as at least one calibrator and, ideally, at least one control. In addition to the calibrators and controls, immunoassays require the use of at least one test sample. Test samples are normally biological samples derived from serum, plasma, whole blood or other bodily fluids (normally from a human patient). The levels of at least one human natriuretic peptide in the test sample is quantified in the immunoassay.

For example, U.S. Pat. No. 6,162,902 (hereinafter referred to as the "'902 patent") discloses isolated antibodies that are monospecifically reactive to epitopes 1-10, 5-13 and 15-25 of Hbnp. More particularly, the '902 patent describes two isolated monoclonal antibodies. The first monoclonal antibody is produced by hybridoma cell line 106.3 (ATCC Accession No. HB 12044) and is monospecifically reactive to epitopes 5-13 of Hbnp. The second monoclonal antibody is produced by hybridoma cell line 201.3 (ATCC Accession No. HB 12045) and is monospecifically reactive to epitopes 1-10 of Hbnp. The '902 patent also describes the use of the above antibodies in immunoassays for the purpose of quantifying the amount of HBNP in a biological sample. U.S. Pat. No. 6,677,124 (hereinafter referred to as the "'124 patent") discloses a monoclonal antibody that binds to an epitope having the amino acid sequence of LYS-VAL-LEU-ARG-ARG-HIS (SEQ ID NO:6) that is found in the C-terminal region of Hbnp, namely epitopes 27-32. More particularly, the '124 patent describes a monoclonal antibody produced by hybridoma cell line BC203 (FERM BP-3515). The '124 patent also describes immunoassays for Hbnp using this monoclonal antibody.

As mentioned briefly previously, one of the problems with natural human natriuretic peptides is that these peptides are unstable in plasma and serum. As also mentioned previously, it is known in the art that both natural and synthetic human BNP is subject to protease cleavage at the amino terminus between amino acids 2-3 and at the carboxy terminus between amino acids 30-32. One of the problems with the immunoassays described in the '902 and '124 patents is that if the Hbnp in the test sample is subject to protease cleavage at either or both of the amino or carboxy terminus that the monoclonal antibodies employed in said immunoassays will be unable to detect Hbnp in the test sample. The failure to detect Hbnp in a test sample could result in a missed or incorrect diagnosis. Therefore, there is a need in the art for antibodies that bind to epitopes in human natriuretic peptides, particularly Hbnp, that are not subject to preotease cleavage, as well as for immunoassays that employ said antibodies.

SUMMARY OF THE INVENTION

In one embodiment, the present invention relates to an antibody or a BNP-antigen binding fragment (also referred to interchangeably herein as a "functionally active" fragment) thereof, such as, but not limited to, a monoclonal antibody or BNP-antigen binding fragment thereof, that specifically binds to an epitope comprising at least a portion of the ring of human BNP (the molecule representing amino acids 77-108 of the 108 amino acid precursor polypeptide of human BNP), wherein said epitope has an amino acid sequence comprising at least three (3) amino acids of amino acids 13-20 of human BNP.

In another embodiment, the present invention relates to an antibody or a BNP-antigen binding fragment thereof, such as, but not limited to, a monoclonal antibody or a BNP-antigen binding fragment thereof, that specifically binds to an epitope comprising at least a portion of the ring of human BNP, wherein said epitope has an amino acid sequence comprising at least amino acid thirteen (arginine), amino acid sixteen (aspartic acid), amino acid seventeen (arginine), and amino acid eighteen (isoleucine) of human BNP.

In another embodiment, the present invention relates to an antibody or a BNP-antigen binding fragment thereof, such as, but not limited to, a monoclonal antibody, that specifically binds to an epitope of human BNP or a human BNP fragment thereof, wherein said epitope of human BNP or human BNP fragment thereof has an amino acid sequence of amino acids 13-20, 13-19, 13-18, 13-17, 13-16, 13-15, 14-20, 14-20, 14-19, 14-18, 14-17, 14-16, 15-20, 15-19, 15-18, 15-17, 16-20, 16-19 or 16-18 of human BNP.

In yet another embodiment, the present invention relates to hybridoma cell line 3-631-436 having A.T.C.C. Accession No. PTA-6476.

In yet another embodiment, the present invention relates to a monoclonal antibody or BNP-antigen binding fragment thereof produced by hybridoma cell line 3-631-436, wherein said cell line has A.T.C.C. Accession No. PTA-6476.

In yet another embodiment, the present invention relates to an immunoassay for human BNP or a fragment of Hbnp. The immunoassay involves the following steps:
(a) contacting at least one antibody or BNP-antigen binding fragment thereof with a test sample suspected of containing or known to contain Hbnp or a Hbnp fragment to form an antibody-Hbnp complex, wherein the antibody or BNP-antigen binding fragment is produced by hybridoma cell line 3-631-436, wherein said cell line has A.T.C.C. Accession No. PTA-6476; and
(b) detecting the formation of the antibody-Hbnp complex.

The above-described immunoassay can further comprise the step of contacting the antibody-Hbnp complex with at least one detection antibody or BNP-antigen binding fragment thereof to form a capture antibody-Hbnp-detection antibody complex, wherein the detection antibody or BNP-antigen binding fragment thereof is conjugated to a detectable label. Alternatively, the immunoassay can further comprise a labeled Hbnp peptide, labeled Hbnp fragment or labeled Hbnp analogue thereof which binds to the antibody or BNP-antigen binding fragment thereof according to the amount or concentration of Hbnp or Hbnp fragment present in the sample. In the above described immunoassay, the amount of the capture-Hbnp-detection antibody complex formed is related to the amount of Hbnp via the use of a standard curve for Hbnp or Hbnp fragment thereof.

In yet still another embodiment, the present invention relates to an immunoassay for human BNP or a Hbnp fragment thereof. The immunoassay involves the following steps:
(a) contacting at least one capture antibody or BNP-antigen binding fragment thereof that binds to Hbnp or a Hbnp fragment thereof with a test sample suspected of containing Hbnp or a Hbnp fragment to form a capture antibody-Hbnp complex, wherein the at least one capture antibody or BNP-antigen binding fragment thereof is a monoclonal antibody or a BNP-antigen binding fragment thereof produced by hybridoma cell line 3-631-436, wherein the cell line has A.T.C.C. Accession No. PTA-6476;
(b) contacting said capture antibody-Hbnp complex with at least one detection antibody or a BNP-antigen binding fragment thereof to form a capture antibody-Hbnp-detection antibody complex, wherein said detection antibody or BNP-antigen binding fragment thereof is conjugated to a detectable label and further wherein said detection antibody or BNP-antigen binding fragment thereof specifically binds to a peptide epitope having an amino acid sequence containing amino acids 5-13 of Hbnp;
(c) determining the amount of capture antibody-Hbnp-detection antibody complexes formed in step (b); and
(d) relating the amount of the capture antibody-Hbnp-detection antibody complexes formed to the amount of Hbnp via use of a standard curve for Hbnp or a Hbnp fragment.

The detection antibody or BNP-antigen binding fragment thereof used in the above-described method can be a monoclonal antibody, such as a monoclonal antibody or a BNP-antigen binding fragment thereof produced by hybridoma cell line 106.3 having A.T.C.C. Accession No. HB 12044. Additionally, the detectable label used in said method can be a radioactive label, an enzymatic label, a chemiluminescent label, a fluorescence label, a thermometric label or an immuno-polymerase chain reaction label.

Optionally, prior to contacting the at least one capture antibody with the test sample, the method can comprise the additional step of immobilizing the at least one capture antibody or BNP-antigen binding fragment thereof onto a solid phase to produce an immobilized first antibody.

In yet still another further embodiment, the present invention relates to immunoassay for human BNP or a Hbnp fragment. The immunoassay comprises the following steps:
(a) contacting at least one capture antibody or BNP-antigen binding fragment thereof that binds to Hbnp or a Hbnp fragment thereof with a test sample suspected of containing Hbnp or a Hbnp fragment to form a capture antibody-Hbnp complex, wherein the at least one capture antibody or BNP-antigen binding fragment thereof is a monoclonal antibody or BNP-antigen binding fragment thereof produced by hybridoma cell line 106.3, wherein said cell line has A.T.C.C. Accession No. HB 12044;

(b) contacting said capture antibody-Hbnp complex with at least one detection antibody or BNP-antigen binding fragment thereof to form a capture antibody-Hbnp-detection antibody complex, wherein said detection antibody or BNP-antigen binding fragment thereof is conjugated to a detectable label and further wherein said detection antibody or BNP-antigen binding fragment thereof is a monoclonal antibody or BNP-antigen binding fragment thereof produced by hybridoma cell line 3-631-436;

(c) determining the amount of capture antibody-Hbnp-detection antibody complexes formed in step (b); and (d) relating the amount of the capture antibody-Hbnp-detection antibody complexes formed to the amount of the Hbnp via use of a standard curve for Hbnp or a Hbnp fragment.

Additionally, the detectable label used in said method can be a radioactive label, an enzymatic label, a chemiluminescent label, a fluorescence label, a thermometric label or an immuno-polymerase chain reaction label.

Optionally, prior to contacting the at least one capture antibody with the test sample, the method can comprise the additional step of immobilizing the at least one capture antibody or BNP-antigen binding fragment thereof on to a solid phase to produce an immobilized first antibody.

In yet another embodiment, the present invention relates to a different immunoassay for human BNP or a Hbnp fragment. This immunoassay comprises the following steps:

(a) immobilizing at least one capture antibody or BNP-antigen binding fragment thereof that binds to Hbnp or a Hbnp fragment onto a solid phase to produce an immobilized first antibody, wherein the at least one capture antibody or BNP-antigen binding fragment thereof is a monoclonal antibody or BNP-antigen binding fragment thereof produced by hybridoma cell line 3-631-436, wherein said cell line has A.T.C.C. Accession No. PTA-6476;

(b) contacting said immobilized capture antibody with a test sample suspected of containing Hbnp or Hbnp fragment to form an first immobilized antibody-Hbnp complex;

(c) contacting said immobilized capture antibody with a Hbnp, a Hbnp fragment or a Hbnp analogue thereof that has been conjugated to a detectable label to form an second immobilized antibody-Hbnp complex, and further wherein the Hbnp fragment or Hbnp analogue has an amino acid sequence comprising amino acids 13-20, 13-19, 13-18, 13-17, 13-16, 13-15, 14-20, 14-20, 14-19, 14-18, 14-17, 14-16, 15-20, 15-19, 15-18, 15-17, 16-20, 16-19 or 16-18 of Hbnp;

(d) determining the amount of detectable label in second immobilized antibody-Hbnp complexes formed in step (c); and (e) relating the amount of the second antibody-Hbnp-antibody complexes formed to the amount of the Hbnp via use of a standard curve for Hbnp or Hbnp fragment.

In yet another embodiment, the present invention relates to yet another different immunoassay for human BNP or a Hbnp fragment. This immunoassay comprises the following steps:

(a) immobilizing a Hbnp, a Hbnp fragment or a Hbnp analogue thereof onto a solid phase to produce immobilized Hbnp, a Hbnp fragment or a Hbnp analogue, wherein the Hbnp fragment or Hbnp analogue has an amino acid sequence comprising amino acids 13-20, 13-19, 13-18, 13-17, 13-16, 13-15, 14-20, 14-20, 14-19, 14-18, 14-17, 14-16, 15-20, 15-19, 15-18, 15-17, 16-20, 16-19 or 16-18 of Hbnp;

(b) contacting said immobilized Hbnp, Hbnp fragment or Hbnp analogue thereof with a test sample suspected of containing Hbnp or a Hbnp fragment;

(c) contacting said immobilized Hbnp, Hbnp fragment or Hbnp analogue thereof and the test sample suspected of containing BNP or a Hbnp fragment with at least one antibody or BNP-antigen binding fragment thereof that has been conjugated to a detectable label to form an immobilized Hbnp-antibody complex and a non-immobilized Hbnp-antibody complex, wherein the antibody or BNP-antigen binding fragment thereof is a monoclonal antibody or BNP-antigen binding fragment thereof produced by hybridoma cell line 3-631-436, wherein said cell line has A.T.C.C. Accession No. PTA-6476;

(d) removing the non-immobilized Hbnp-antibody complex;

(e) determining the amount of immobilized Hbnp-antibody complex formed in step (c); and (f) relating the amount of the immobilized Hbnp-antibody complex formed to the amount of the Hbnp via use of a standard curve for Hbnp or a Hbnp fragment.

In yet still another embodiment, the present invention relates to an immunoassay for human BNP (Hbnp) or Hbnp fragment. the immunoassay comprising the steps of:

(a) contacting at least one antibody or BNP-antigen binding fragment thereof with a test sample suspected of containing Hbnp or a Hbnp fragment to form a Hbnp-antibody complex, wherein the antibody or BNP-antigen binding fragment thereof is a monoclonal antibody or BNP-antigen binding fragment thereof produced by hybridoma cell line 3-631-436, wherein said cell line has A.T.C.C. Accession No. PTA-6476;

(b) contacting said Hbnp-antibody complex with a labeled Hbnp peptide, Hbnp fragment, or Hbnp analogue thereof, wherein the labeled Hbnp fragment or Hbnp analogue thereof has an amino acid sequence comprising amino acids 13-20, 13-19, 13-18, 13-17, 13-16, 13-15, 14-20, 14-19, 14-18, 14-17, 14-16, 15-20, 15-19, 15-18, 15-17, 16-20, 16-19 or 16-18 of Hbnp;

(c) determining the amount of labeled Hbnp-antibody complex formed; and (d) relating the amount of the labeled Hbnp-antibody complex formed to the amount of Hbnp in the sample via use of a standard curve.

In yet another embodiment, the present invention relates to yet another different immunoassay for human BNP or a Hbnp fragment. This immunoassay comprises the following steps:

(a) contacting at least one antibody or BNP-antigen binding fragment thereof with a test sample suspected of containing Hbnp or a Hbnp fragment thereof and a labeled Hbnp peptide, Hbnp fragment, or Hbnp analogue thereof to form labeled Hbnp-antibody complexes and unlabeled Hbnp-antibody complexes, wherein the antibody or BNP-antigen binding fragment thereof is a monoclonal antibody or BNP-antigen binding fragment thereof produced by hybridoma cell line 3-631-436, wherein said cell line has A.T.C.C. Accession No. PTA-6476 and further wherein the labeled Hbnp fragment or Hbnp analogue thereof has an amino acid sequence comprising amino acids 13-20, 13-19, 13-18, 13-17, 13-16, 13-15, 14-20, 14-19, 14-18, 14-17, 14-16, 15-20, 15-19, 15-18, 15-17, 16-20, 16-19 or 16-18 of Hbnp;

(b) determining the amount of labeled Hbnp-antibody complexes formed; and (c) relating the amount of the labeled Hbnp-antibody complexes formed to the amount of Hbnp via use of a standard curve.

In yet another embodiment, the present invention relates to yet another different immunoassay for human BNP or a Hbnp fragment. This immunoassay comprises the following steps:

(a) contacting at least one antibody or BNP-antigen binding fragment thereof with a labeled Hbnp peptide, Hbnp fragment, or Hbnp analogue thereof to form a labeled Hbnp-antibody complex, wherein the antibody or BNP-antigen binding fragment thereof is a monoclonal antibody or BNP-antigen binding fragment thereof produced by hybridoma cell line 3-631-436, wherein said cell line has A.T.C.C. Accession No. PTA-6476 and further wherein the labeled Hbnp fragment or Hbnp analogue thereof has an amino acid sequence comprising amino acids 13-20, 13-19, 13-18, 13-17, 13-16, 13-15, 14-20, 14-19, 14-18, 14-17, 14-16, 15-20, 15-19, 15-18, 15-17, 16-20, 16-19 or 16-18 of Hbnp;

(b) contacting said labeled Hbnp-antibody complex with a test sample suspected of containing BNP or Hbnp fragment;

(c) determining the amount of labeled Hbnp-antibody complex formed; and (d) relating the amount of the labeled Hbnp-antibody complex formed to the amount of Hbnp in the sample via use of a standard curve.

DETAILED DESCRIPTION OF THE INVENTION

I. Background

Figure 1:
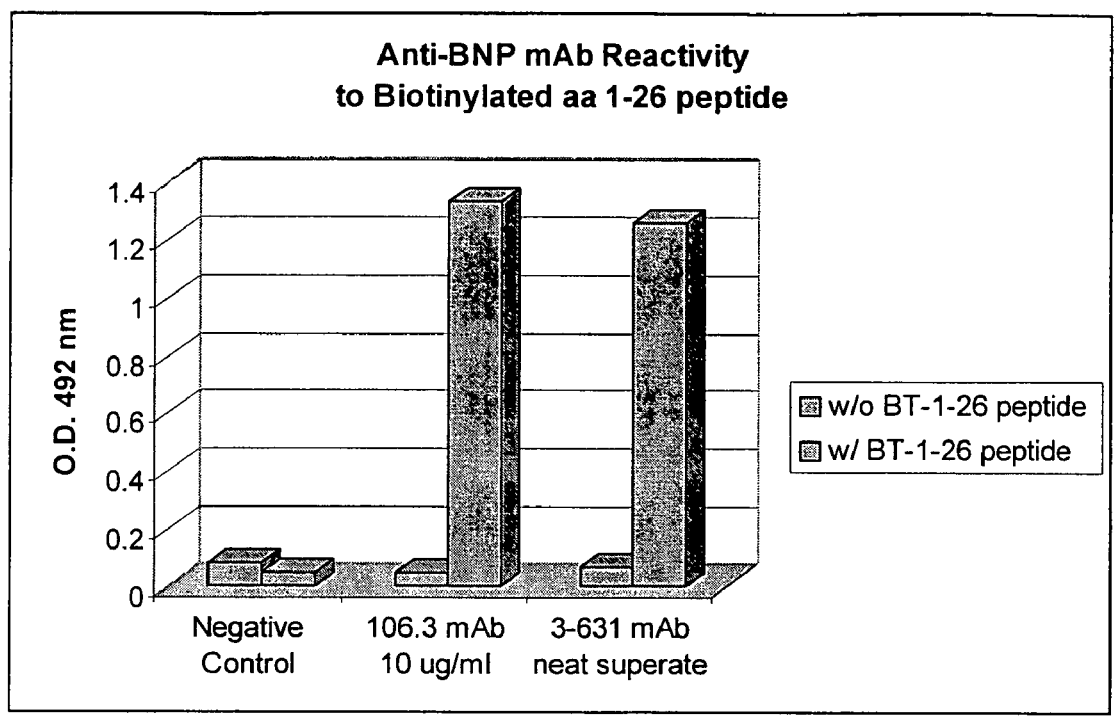
FIG. 1 shows an indirect enzyme immunoassay (hereafter "EIA") conducted using a biotinylated Hbnp peptide fragment (containing amino acids 1-26) and a monoclonal antibody produced from hybridoma cell line 3-631-435 and a monoclonal antibody produced from hybridoma cell line 106.3.

Briefly, in one embodiment, the present invention relates to novel antibodies that specifically bind to an epitope having an amino acid sequence comprising at least three (3) amino acids of amino acids 13-20 of Hbnp or an epitope having an amino acid sequence comprising at least three (3) amino acids of amino acids 17-24 of Hbnp. The antibodies of the present invention are highly sensitive reagents and are useful in the qualitative and/or quantitative detection of Hbnp or a Hbnp fragment in test samples. In a second embodiment, the present invention relates to immunoassays that employ the antibodies of the present invention.

As used herein, the term "human BNP", "Hbnp", "Hbnp peptide" or "Hbnp polypeptide" refers to a 32 amino acid molecule representing amino acids 77-108 of the 108 amino acid precursor molecule of human brain natriuretic peptide. The term "Hbnp fragment" or "Hbnp peptide fragment" as used herein refers to a polypeptide that comprises at least five contiguous amino acids of amino acids 77-108 of the 108 amino acid BNP precursor molecule. In preferred embodiments, a Hbnp fragment or Hbnp peptide fragment refers to a polypeptide that comprises at least ten contiguous amino acids of amino acids 77-108 of the 108 amino acid BNP precursor molecule; at least fifteen contiguous amino acids of amino acids 77-108 of the 108 amino acid BNP precursor molecule; at least 20 contiguous amino acids of amino acids 77-108 of the 108 amino acid BNP precursor molecule; at least 25 contiguous amino acids of amino acids 77-108 of the 108 amino acid BNP precursor molecule. Examples of Hbnp fragments or Hbnp peptide fragments include, but are not limited to, amino acid sequences containing amino acids 1-31, 1-30, 1-29, 1-28, 1-27, 1-26, 1-25, 1-24, 1-23, 1-22, 1-21, 1-20, 1-19, 1-18, 1-17, 1-16, 1-15, 2-32, 2-31, 2-30, 2-29, 2-28, 2-27, 2-26, 2-25, 2-24, 2-23, 2-22, 2-21, 2-20, 2-19, 2-18, 2-17, 2-16, 2-15, 3-32, 3-31, 3-30, 3-29, 3-28, 3-27, 3-26, 3-25, 3-24, 3-23, 3-32, 3-21, 3-20, 3-19, 3-18, 3-17, 3-16, 3-15, 4-32, 4-31, 4-30, 4-29, 4-28, 4-27, 4-26, 4-25, 4-24, 4-23, 4-22, 4-21, 4-20, 4-19, 4-18, 4-17, 4-16, 4-15, 5-32, 5-31, 5-30, 5-29, 5-28, 5-27, 5-26, 5-25, 5-24, 5-23, 5-22, 5-21, 5-20, 5-19, 5-18, 5-17, 5-16, 5-15, 6-32, 6-31, 6-30, 6-29, 6-28, 6-27, 6-26, 6-25, 6-24, 6-23, 6-22, 6-21, 6-20, 6-19, 6-18, 6-17, 6-16, 6-15, 7-32, 7-31, 7-30, 7-29, 7-28, 7-27, 7-26, 7-25, 7-24, 7-23, 7-22, 7-21, 7-20, 7-19, 7-18, 7-17, 7-16, 7-15, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 9-32, 9-31, 9-30, 9-29, 9-28, 9-27, 9-26, 9-25, 9-24, 9-23, 9-22, 9-21, 9-20, 9-19, 9-18, 9-17, 9-16, 9-15, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 11-32, 11-31, 11-30, 11-29, 11-28, 11-27, 11-26, 11-25, 11-24, 11-23, 11-22, 11-21, 11-20, 11-19, 11-18, 11-17, 11-16, 11-15, 12-32, 12-31, 12-30, 12-29, 12-28, 12-27, 12-26, 12-25, 12-24, 12-23, 12-22, 12-21, 12-20, 12-19, 12-18, 12-17, 12-16, 13-32, 13-31, 13-30, 13-29, 13-28, 13-27, 13-26, 13-25, 13-24, 13-23, 13-22, 13-21, 13-20, 13-19, 13-18, 13-17, 14-32, 14-31, 14-30, 14-29, 14-28, 14-27, 14-26, 14-25, 14-24, 14-23, 14-22, 14-21, 14-20, 14-19, 14-18, 15-32, 15-31, 15-30, 15-29, 15-28, 15-27, 15-26, 15-25, 15-24, 15-23, 15-22, 15-21, 15-20, 15-19, 16-32, 16-31, 16-30, 16-29, 16-28, 16-27, 16-26, 16-25, 16-24, 16-23, 16-22, 16-21, 16-20, 17-32, 17-31, 17-30, 17-29, 17-28, 17-27, 17-26, 17-25, 17-24, 17-23, 17-22, 17-21, 18-32, 18-31, 18-30, 18-29, 18-28, 18-27, 18-26, 18-25, 18-24, 18-23, 18-22, 19-32, 19-31, 19-30, 19-29, 19-28, 19-27, 19-28, 19-27, 19-26, 19-25, 19-24 or 19-23 of Hbnp.

II. Antibodies of the Present Invention

As discussed briefly above, in one embodiment, the present invention relates to highly sensitive reagents that preferably allow for the rapid, simple, accurate and qualitative and/or quantitative detection of Hbnp or a Hbnp fragment in a test sample. As used herein, the term "test sample" refers to a biological sample derived from serum, plasma, whole blood, lymph, CNS fluid, urine or other bodily fluids of a mammal, typically a human. The test sample can be prepared using routine techniques known in the art.

As used herein, the term "epitope" refers to a portion of an antigen to which B and/or T cells respond. Epitopes can be formed both from contiguous amino acids or noncontiguous amino acids juxtaposed by tertiary folding of a protein. An epitope typically includes at least 3, and more usually, at least 5 or at least 8 amino acids in a unique spatial conformation. Amino acids of an epitope that are important for antibody fragment:antigen binding can be determined by conventional methods which include, but are not limited to, site-directed and regional-selective mutagenesis coupled with determinations of binding affinity between the antibody and antigen. The spatial conformation of an epitope can be determined by conventional methods, which include, for example, x-ray crystallography and 2-dimensional nuclear magnetic resonance. See, e.g., Epitope Mapping Protocols in METHODS IN MOLECULAR BIOLOGY, Vol. 66, Glenn E. Morris, ed (1996).

The inventors have discovered highly stable epitopes within Hbnp and produced antibodies that specifically bind to these regions. An antibody "specifically binds" if its affinity for its intended target (namely, a linear human BNP or a cyclic human BNP comprising at least three amino acids of amino acids 13-20 or 17-24 of human BNP) is about 2-fold greater, preferably about 3-fold greater, more preferably about 4-fold greater, when compared to its affinity for a non-target molecule (namely, a linear human BNP or cyclic human BNP that does not contain at least three amino acids of amino acids 13-20 or 17-24 of human BNP). In preferred embodiments, specific binding between an antibody or other binding agent and an antigen means a binding affinity of at least, $10^8$ $M^{-1}$, preferably at least $10^9$ to $10^{10}$ $M^{-1}$ (for cyclic human BNP comprising at least three amino acids of amino acids 13-20 or 17-24 of human BNP) or a binding affinity of at least $10^6$ to $10^8$ $M^{-1}$ (for linear human BNP comprising at least three amino acids of amino acids 13-20 or 17-24 of human BNP). The present invention provides antibodies and functionally active fragments thereof that specifically bind to any epitope having an amino acid sequence that comprises at least three (3) amino acids of amino acids 13-20 or 17-24 of Hbnp, such as, monoclonal antibodies, that specifically bind to an epitope having an amino acid sequence that includes and is between amino acids 13-20, 13-19, 13-18, 13-17, 13-16, 13-15, 14-20, 14-19, 14-18, 14-17, 14-16, 15-20, 15-19, 15-18, 15-17, 16-20, 16-19, 16-18, 17-24, 17-23, 17-22, 17-21, 17-20, 17-19, 18-24, 18-23, 18-22, 18-21, 18-20, 19-24, 19-23, 19-22 or 19-21 of Hbnp. One skilled in the art will appreciate that one or more of the amino acid residues comprising the epitopes described herein can be changed or substituted without diminishing the ability of an antibody to specifically bind to the epitopes described herein. For example, if the epitope contains amino acids 13-20 of Hbnp, it is expected that at least one of these eight (8) amino acid residues could be replaced by one or more other amino acid residues without significantly diminishing the specificity and affinity of the antibodies (or portions thereof) for the epitope. Such altered epitopes can be used as, among other things, calibrators, controls, or standards for an immunoassay.

The antibodies of the present invention bind to the ring (amino acids 10-26 of Hbnp) of Hbnp. Because the antibodies of the present invention specifically bind to the ring portion of Hbnp, the antibodies of the present invention are not affected by any cleavage that occurs to Hbnp as a result of proteases. Therefore, the antibodies of the present invention can be used in immunoassays and provide a more stable (i.e., improved binding to protealytically cleaved human BNP), detectable signal than other antibodies known in the art.

The antibodies of the present invention can be monoclonal antibodies, polyclonal antibodies, etc. The monoclonal antibodies of the present invention also include "chimeric" and "humanized" antibodies. With chimeric antibodies a portion of the heavy and/or light chain is identical with or homologous to a corresponding sequence in the antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (See U.S. Pat. No. 4,816,567 and Morrison et al., *Proc. Natl. Acad. Sci. USA,* 81:6851-6855 (1984)). Chimeric antibodies of interest include "primatized" antibodies comprising variable domain antigen-binding sequences derived from a non-human primate (such as an Old World Monkey, Ape, etc.) and human constant region sequences. Chimeric antibodies also bring a benefit of reduced false positives that are characterized as human anti-mouse antibody (HAMA) response (See S. J. Thorpe, et al., *Scandinavian Journal of Immunology,* 57:85-92 (2003)).

Additionally, the monoclonal antibodies of the present invention also include "humanized" antibodies. "Humanized" antibodies are non-human (such as rodent) chimeric antibodies that contain a minimal sequence derived from a non-human antibody. For the most part, humanized antibodies are human immunoglobulins (a recipient antibody) in which residues from a hypervariable region of the recipient are replaced by residues from a hypervariable region of a non-human species (a donor antibody), such as a mouse, rat, rabbit or non-human primate, having the desired antibody specificity, affinity and capability. In some instances, framework region residues of the human immunoglobulin are replaced by corresponding non-human residues. Additionally, humanized antibodies may comprise residues that are not found in the recipient antibody or in the donor antibody. These modifications can be made to further refine antibody performance. In general, a humanized antibody will comprise substantially all of at least one, and typically two, variable domains, in which all or substantially all of the hypervariable loops correspond to those of a non-human immunoglobulin and all or substantially all of the hypervariable loops correspond to those of a non-human immunoglobulin and all or substantially all of the FRs are those of a human immunoglobulin sequence. The humanized antibody can optionally comprise at least a portion of an immunoglobulin constant region (Fc), typically that of a human immunoglobulin.

As mentioned above, the antibodies of the present invention can be monoclonal antibodies. Monoclonal antibodies of the present invention can be produced by hybridoma cells prepared pursuant to methods known in the art, particularly those by Kohler, G. and Milstein., C., *Nature,* 256:495 (1975). Generally, mice are immunized with the full length Hbnp peptide containing amino acids 1-32 or an immunogenic conjugate of Hbnp and a suitable partner, such as bovine serum albumin. Periodic booster injections are administered until good antibody titers are achieved. Spleen cells from the immunized mice are then fused with myeloma cells using routine techniques known in the art (See Galfre et al., *Nature,* 266:550 (1977)) to produce hybridoma cells. Supernatants from the hybridoma cell cultures are screened for reactivity to Hbnp. Hybridomas testing positive are recloned and their supernatants retested for reactivity. Using this procedure, as described in more detail in the Examples, the inventors obtained hybridoma cell line 3-631-436, which secretes monoclonal antibodies that specifically recognize Hbnp fragments having an amino acid sequence comprising amino acids 13-20.

Once a highly immunogenic epitope has been identified, non-monoclonal antibodies can be produced from polyclonal antisera. Polyclonal antisera is produced according to routine techniques known in the art. Specifically, a suitable animal, such as a rabbit, is immunized with a Hbnp peptide containing amino acids 1-32 or an immunogenic conjugate of Hbnp and a suitable partner. Periodic booster injections are administered until good antibody titers are achieved. By testing the antisera obtained for immunoreactivity against various peptide fragments of Hbnp, desirable epitopes can be identified. Once a highly stable epitope, such as an epitope having an amino acid sequence comprising at least three (3) amino acids of amino acids 13-20 or 17-24 of Hbnp, is identified, antibodies that specifically bind to this epitope can be obtained by affinity purification of the polyclonal serum on an affinity column using a peptide fragment of Hbnp that contains the epitope having an amino acid sequence containing (including and between) at least three (3) amino acids of amino acids 13-20 or 17-24 of Hbnp and no other epitopes (which can be identified in epitope mapping) and is bound to a solid support. The identified antibody, the nucleic acid producing the antibody, and/or the cell producing the antibody optionally can also be engineered after it is identified, for by site-specific or region-specific mutagenesis, phage display, yeast display, and other techniques known in the art.

Functionally active fragments of the antibodies of the present invention (also referred to interchangeably herein as "BNP-antigen binding fragments") are also contemplated herein and can also be used in the immunoassays described herein. "Functionally active fragments of the antibodies of the present invention retain the immunologic specificity of the antibody, although the selectivity, avidity and/or affinity may not be identical. Functionally active fragments include but are not limited to immunoglobulin fragments such as Fab, F(ab')$_2$ and Fab'. These fragments can be produced using techniques known in the art (such as, e.g., by the enzymatic cleavage of the antibodies (See Mariani et al., *Mol. Immunol.,* 28:69-77 (1991); Ishikawa et al., *J. Immunoassay,* 4:209-327 (1983)).

III. Immunoassays of the Present Invention

In another embodiment, the present invention relates to immunoassays that can be used for the qualitative and/or quantification of Hbnp or a Hbnp fragment in a test sample. The immunoassays of the present invention can be conducted using any format known in the art, preferably, a sandwich format, in a competitive inhibition format (including both forward or reverse competitive inhibition assays) or in a fluorescence polarization format.

In immunoassays for the qualitative detection of Hbnp or a Hbnp fragment in a test sample, at least one antibody or a functionally active fragment that binds to certain epitopes of Hbnp or a Hbnp fragment thereof is contacted with at least one test sample suspected of containing or is known to contain Hbnp or a Hbnp fragment to form an antibody-Hbnp immune complex. This immune complex is then detected using routine techniques in the art. For example, a second antibody that binds to the Hbnp or a Hbnp fragment and that contains a detectable label can be added to the test sample and used to detect the presence of the antibody-Hbnp complex. Any detectable label known in the art can be used. Detectable labels and their attachment to antibodies are discussed in more detail infra.

Preferably, the antibody used in such qualitative immunoassays specifically binds to an epitope having an amino acid sequence comprising at least three (3) amino acids of amino acids 13-20 or 17-24 of Hbnp or to an epitope having an amino acid sequence containing (meaning including and between) amino acids 13-20, 13-19, 13-18, 13-17, 13-16, 14-20, 14-19, 14-18, 14-17, 14-16, 15-20, 15-19, 15-18, 16-20, 16-19, 17-24, 17-23, 17-22, 17-21, 17-20, 17-19, 18-24, 18-23, 18-22, 18-21, 18-20, 19-24, 19-23, 19-22 or 19-21 of Hbnp. An example of an antibody that specifically binds to epitopes having an amino acid sequence containing at least three (3) amino acids of amino acids 13-20 of Hbnp is a monoclonal antibody produced by hybridoma cell line 3-631-436.

In immunoassays for the quantitative detection of BNP, such as a sandwich type format, at least two antibodies are employed to separate and quantify Hbnp or a Hbnp fragment in a test sample. More specifically, the at least two antibodies bind to certain epitopes of Hbnp or Hbnp fragment forming an immune complex which is referred to as a "sandwich". Generally, one or more antibodies can be used to capture the Hbnp in the test sample (these antibodies are frequently referred to as a "capture" antibody or "capture" antibodies) and one or more antibodies is used to bind a detectable (namely, quantifiable) label to the sandwich (these antibodies are frequently referred to as the "detection" antibody or "detection" antibodies). In a sandwich assay, it is preferred that both antibodies binding to their epitope are not diminished by the binding of any other antibody in the assay to its respective epitope. In other words, antibodies should be selected so that the one or more first antibodies brought into contact with a test sample suspected of containing Hbnp or a Hbnp fragment do not bind to all or part of an epitope recognized by the second or subsequent antibodies, thereby interfering with the ability of the one or more second detection antibodies to bind to the Hbnp or Hbnp fragment.

The inventors have discovered that an excellent immunoassay can be performed using a first monoclonal antibody that specifically binds to epitopes comprising at least three (3) amino acids of amino acids 13-20 or 17-24 of Hbnp and a second monoclonal antibody that specifically binds to epitopes having an amino acid sequence containing amino acids 5-13 of Hbnp. An example of a monoclonal antibody that specifically binds to epitopes having an amino acid sequence containing at least three (3) amino acids of amino acids 13-20 of Hbnp is a monoclonal antibody produced by hybridoma cell line 3-631-436. An example of a monoclonal antibody that specifically binds to epitopes having an amino acid sequence containing amino acids 5-13 of Hbnp is a monoclonal antibody produced by hybridoma cell line 106.3.

More specifically, the inventors have produced a sandwich type assay that is highly sensitive and employs a monoclonal antibody produced by hybridoma cell line 3-631-436 as the capture antibody (See Example 8).

In a preferred embodiment, the test sample suspected of containing Hbnp or a Hbnp fragment can be contacted with at least one first capture antibody (or antibodies) and at least one second detection antibodies either simultaneously or sequentially. In the sandwich assay format, a test sample suspected of containing Hbnp or Hbnp fragment is first brought into contact with the at least one first capture antibody that specifically binds to a particular epitope under conditions which allow the formation of a first antibody-Hbnp complex. If more than one capture antibody is used, a first multiple capture antibody-Hbnp complex is formed. In a sandwich assay, the antibodies, preferably, the at least one capture antibody, are used in molar excess amounts of the maximum amount of Hbnp or Hbnp fragment expected in the test sample. For example, from about 5 µg/Ml to about 1 mg/Ml of antibody per Ml of microparticle coating buffer can be used.

Optionally, prior to contacting the test sample with the at least one first capture antibody, the at least one first capture antibody can be bound to a solid support which facilitates the separation the first antibody-Hbnp complex from the test sample. Any solid support known in the art can be used, including but not limited to, solid supports made out of polymeric materials in the forms of wells, tubes or beads. The antibody (or antibodies) can be bound to the solid support by adsorption, by covalent bonding using a chemical coupling agent or by other means known in the art, provided that such binding does not interfere with the ability of the antibody to bind Hbnp or Hbnp fragment. Moreover, if necessary, the solid support can be derivatized to allow reactivity with various functional groups on the antibody. Such derivatization requires the use of certain coupling agents such as, but not limited to, maleic anhydride, N-hydroxysuccinimide and 1-ethyl-3-(3-dimethylaminopropyl)carbodiimide.

After the test sample suspected of containing Hbnp or an Hbnp fragment is brought into contact with the at least one first capture antibody, the test sample is incubated in order to allow for the formation of a first capture antibody (or multiple antibody)-Hbnp complex. The incubation can be carried out at a Ph of from about 4.5 to about 10.0, at a temperature of from about 2° C. to about 45° C., and for a period from at least about one (1) minute to about eighteen (18) hours, preferably from about 2-6 minutes, most preferably from about 3-4 minutes.

After formation of the first/multiple capture antibody-Hbnp complex, the complex is then contacted with at least one second detection antibody (under conditions which allow for the formation of a first/multiple antibody-Hbnp-second antibody complex). If the first antibody-Hbnp complex is contacted with more than one detection antibody, then a first/multiple capture antibody-Hbnp-multiple antibody detection complex is formed. As with first antibody, when the at least second (and subsequent) antibody is brought into contact with the first antibody-Hbnp complex, a period of incubation under conditions similar to those described above is required for the formation of the first/multiple antibody-Hbnp-second/multiple antibody complex. Preferably, at least one second antibody contains a detectable label. The detectable label can be bound to the at least one second antibody prior to, simultaneously with or after the formation of the first/multiple antibody-Hbnp-second/multiple antibody complex. Any detectable label known in the art can be used. For example, the detectable label can be a radioactive label, such as, $^3$H, $^{125}$I, $^{35}$S, $^{14}$C, $^{32}$P, $^{33}$P, an enzymatic label, such as horseradish peroxidase, alkaline peroxidase, glucose 6-phosphate dehydrogenase, etc., a chemiluminescent label, such as, acridinium esters, luminal, isoluminol, thioesters, sulfonamides, phenanthridinium esters, etc. a fluorescence label, such as, fluorescein (5-fluorescein, 6-carboxyfluorescein, 3'6-carboxyfluorescein, 5(6)-carboxyfluorescein, 6-hexachlorofluorescein, 6-tetrachlorofluorescein, fluorescein isothiocyanate, etc.), rhodamine, phycobiliproteins, R-phycoerythrin, quantum dots (zinc sulfide-capped cadmium selenide), a thermometric label or an immuno-polymerase chain reaction label. An introduction to labels, labeling procedures and detection of labels is found in Polak and Van Noorden, *Introduction to Immunocytochemistry*, $2^{nd}$ ed., Springer Verlag, N.Y. (1997) and in Haugland, *Handbook of Fluorescent Probes and Research Chemicals* (1996), which is a combined handbook and catalogue published by Molecular Probes, Inc., Eugene, Oreg.

The detectable label can be bound to the antibodies either directly or through a coupling agent. An example of a coupling agent that can be used is EDAC (1-ethyl-3-(3-dimethylaminopropyl)carbodiimide, hydrochloride) that is commercially available from Sigma-Aldrich, St. Louis, Mo. Other coupling agents that can be used are known in the art. Methods for binding a detectable label to an antibody are known in the art. Additionally, many detectable labels can be purchased or synthesized that already contain end groups that facilitate the coupling of the detectable label to the antibody, such as, N10-(3-sulfopropyl)-N-(3-carboxypropyl)-acridinium-9-carboxamide, otherwise known as CPSP-Acridinium Ester or N10-(3-sulfopropyl)-N-(3-sulfopropyl)-acridinium-9-carboxamide, otherwise known as SPSP-Acridinium Ester.

The first antibody/multiple-Hbnp-second/multiple antibody complex can be, but does not have to be, separated from the remainder of the test sample prior to quantification of the label. For example, if the at least first capture antibody is bound to a solid support, such as a well or a bead, separation can be accomplished by removing the fluid (from the test sample) from contact with the solid support. Alternatively, if the at least first capture antibody is bound to a solid support it can be simultaneously contacted with the Hbnp-containing sample and the at least one second detection antibody to form a first (multiple) antibody-Hbnp-second (multiple) antibody complex, followed by removal of the fluid (test sample) from contact with the solid support. If at least first capture antibody is not bound to a solid support, then the first antibody/multiple-Hbnp-second/multiple antibody complex does not have to be removed from the test sample for quantification of the amount of the label.

After formation of the labeled first antibody-Hbnp-second antibody complex, the amount of label in the complex is quantified using techniques known in the art. For example, if an enzymatic label is used, the labeled complex is reacted with a substrate for the label that gives a quantifiable reaction such as the development of color. If the label is a radioactive label, the label is quantified using a scintillation counter. If the label is a fluorescent label, the label is quantified by stimulating the label with a light of one color (which is known as the "excitation wavelength") and detecting another color (which is known as the "emission wavelength") that is emitted by the label in response to the stimulation. If the label is a chemiluminescent label, the label is quantified detecting the light emitted either visually or by using luminometers, x-ray film, high speed photographic film, a CCD camera, etc. Once the amount of the label in the complex has been quantified, the concentration of Hbnp or Hbnp fragment in the test sample is determined by use of a standard curve that has been generated using serial dilutions of Hbnp or Hbnp fragment of known concentration. Other than using serial dilutions of Hbnp or Hbnp fragment, the standard curve can be generated gravimetrically, by mass spectroscopy and by other techniques known in the art.

In a forward competitive format, an aliquot of labeled Hbnp, Hbnp fragment or Hbnp analogue thereof of a known concentration is used to compete with Hbnp or Hbnp fragment in a test sample for binding to Hbnp antibody (such as a monoclonal antibody produced by hybridoma cell line 3-631-436). Peptides of Hbnp, Hbnp fragments and Hbnp analogues thereof and methods of making peptides of Hbnp, Hbnp fragments and Hbnp analogues are known in the art (See, for example, U.S. Pat. No. 6,162,902).

In a forward competition assay, an immobilized antibody (such as a monoclonal antibody produced by hybridoma cell line 3-631-436) can either be sequentially or simultaneously contacted with the test sample and a labeled Hbnp, Hbnp fragment or Hbnp analogue thereof. The Hbnp peptide, Hbnp fragment or Hbnp analogue can be labeled with any detectable label known to those skilled in the art, including those detectable labels discussed above in connection with the sandwich assay format.

The labeled Hbnp peptide, Hbnp fragment or Hbnp analogue, the test sample and the antibody are incubated under conditions similar to those described above in connection with the sandwich assay format. Two different species of antibody-Hbnp complexes are then generated. Specifically, one of the antibody-Hbnp complexes generated contains a detectable label while the other antibody-Hbnp complex does not contain a detectable label. The antibody-Hbnp complex can be, but does not have to be, separated from the remainder of the test sample prior to quantification of the detectable label. Regardless of whether the antibody-Hbnp complex is separated from the remainder of the test sample, the amount of detectable label in the antibody-Hbnp complex is then quantified. The concentration of Hbnp or Hbnp fragment in the test sample can then be determined by comparing the quantity of detectable label in the antibody-Hbnp complex to a standard curve. The standard curve can be generated using serial dilutions of Hbnp or Hbnp fragment of known concentration, by mass spectroscopy, gravimetrically and by other techniques known in the art.

The antibody-Hbnp complex can be separated from the test sample by binding the antibody to a solid support, such as the solid supports discussed above in connection with the sandwich assay format, and then removing the remainder of the test sample from contact with the solid support.

The labeled Hbnp (or Hbnp fragment or Hbnp analogue thereof) that is used to compete with Hbnp or a Hbnp fragment in the test sample for binding to the antibody can be intact Hbnp 1-32, any Hbnp fragment thereof provided that said Hbnp fragment comprises at least one amino acid sequence containing (meaning including and between) amino acids 13-20, 13-19, 13-18, 13-17, 13-16, 13-15, 14-20, 14-19, 14-18, 14-17, 14-16, 15-20, 15-19, 15-18, 15-17, 16-20, 16-19, 16-18, 17-24, 17-23, 17-22, 17-21, 17-20, 17-19, 18-24, 18-23, 18-22, 18-21, 18-20, 19-24, 19-23, 19-22 or 19-21 of Hbnp) or any Hbnp analogue provided that said Hbnp peptide, Hbnp fragment or Hbnp analogue contains a sequence of amino acids that corresponds to an epitope that is recognized by the antibody. Preferably, the antibody employed specifically binds to an epitope comprising at least three (3) amino acids of amino acids 13-20 or 17-24 of Hbnp (such as the monoclonal antibody produced by hybridoma cell line 3-631-436) or specifically binds to an epitope having an amino acid sequence that contains (meaning that it includes and is between) amino acids 13-20, 13-19, 13-18, 13-17, 13-16, 13-15, 14-20, 14-19, 14-18, 14-17, 14-16, 15-20, 15-19, 15-18, 15-17, 16-20, 16-19, 16-18, 17-24, 17-23, 17-22, 17-21, 17-20, 17-19, 18-24, 18-23, 18-22, 18-21, 18-20, 19-24, 19-23, 19-22 or 19-21 of Hbnp.

Examples of Hbnp fragments that can be labeled and used in the present invention, include, but are not limited to, peptide fragments having an amino acid sequence containing amino acids 1-31, 1-30, 1-29, 1-28, 1-27, 1-26, 1-25, 1-24, 1-23, 1-22, 1-21, 1-20, 1-19, 1-18, 1-17, 1-16, 1-15, 2-32, 2-31, 2-30, 2-29, 2-28, 2-27, 2-26, 2-25, 2-24, 2-23, 2-22, 2-21, 2-20, 2-19, 2-18, 2-17, 2-16, 2-15, 3-32, 3-31, 3-30, 3-29, 3-28, 3-27, 3-26, 3-25, 3-24, 3-23, 3-32, 3-21, 3-20, 3-19, 3-18, 3-17, 3-16, 3-15, 4-32, 4-31, 4-30, 4-29, 4-28, 4-27, 4-26, 4-25, 4-24, 4-23, 4-22, 4-21, 4-20, 4-19, 4-18, 4-17, 4-16, 4-15, 5-32, 5-31, 5-30, 5-29, 5-28, 5-27, 5-26, 5-25, 5-24, 5-23, 5-22, 5-21, 5-20, 5-19, 5-18, 5-17, 5-16, 5-15, 6-32, 6-31, 6-30, 6-29, 6-28, 6-27, 6-26, 6-25, 6-24, 6-23, 6-22, 6-21, 6-20, 6-19, 6-18, 6-17, 6-16, 6-15, 7-32, 7-31, 7-30, 7-29, 7-28, 7-27, 7-26, 7-25, 7-24, 7-23, 7-22, 7-21, 7-20, 7-19, 7-18, 7-17, 7-16, 7-15, 8-32, 8-31, 8-30, 8-29, 8-28, 8-27, 8-26, 8-25, 8-24, 8-23, 8-22, 8-21, 8-20, 8-19, 8-18, 8-17, 8-16, 8-15, 9-32, 9-31, 9-30, 9-29, 9-28, 9-27, 9-26, 9-25, 9-24, 9-23, 9-22, 9-21, 9-20, 9-19, 9-18, 9-17, 9-16, 9-15, 10-32, 10-31, 10-30, 10-29, 10-28, 10-27, 10-26, 10-25, 10-24, 10-23, 10-22, 10-21, 10-20, 10-19, 10-18, 10-17, 10-16, 10-15, 11-32, 11-31, 11-30, 11-29, 11-28, 11-27, 11-26, 11-25, 11-24, 11-23, 11-22, 11-21, 11-20, 11-19, 11-18, 11-17, 11-16, 11-15, 12-32, 12-31, 12-30, 12-29, 12-28, 12-27, 12-26, 12-25, 12-24, 12-23, 12-22, 12-21, 12-20, 12-19, 12-18, 12-17, 12-16, 13-32, 13-31, 13-30, 13-29, 13-28, 13-27, 13-26, 13-25, 13-24, 13-23, 13-22, 13-21, 13-20, 13-19, 13-18, 13-17, 14-32, 14-31, 14-30, 14-29, 14-28, 14-27, 14-26, 14-25, 14-24, 14-23, 14-22, 14-21, 14-20, 14-19, 14-18, 15-32, 15-31, 15-30, 15-29, 15-28, 15-27, 15-26, 15-25, 15-24, 15-23, 15-22, 15-21, 15-20, 15-19, 16-32, 16-31, 16-30, 16-29, 16-28, 16-27, 16-26, 16-25, 16-24, 16-23, 16-22, 16-21, 16-20, 17-32, 17-31, 17-30, 17-29, 17-28, 17-27, 17-26, 17-25, 17-24, 17-23, 17-22, 17-21, 18-32, 18-31, 18-30, 18-29, 18-28, 18-27, 18-26, 18-25, 18-24, 18-23, 18-22, 19-32, 19-31, 19-30, 19-29, 19-28, 19-27, 19-28, 19-27, 19-26, 19-25, 19-24 or 19-23 of Hbnp.

In a reverse competition assay, an immobilized Hbnp peptide, Hbnp fragment or Hbnp analogue thereof can either be sequentially or simultaneously contacted with a test sample and at least one labeled antibody. Preferably, the antibody specifically binds to an epitope having an amino acid sequence comprising at least three (3) amino acids of amino acids 13-20 or 17-24 of Hbnp or to an epitope having an amino acid sequence containing (meaning including and between) amino acids 13-20, 13-19, 13-18, 13-17, 13-16, 14-20, 14-19, 14-18, 14-17, 14-16, 15-20, 15-19, 15-18, 16-20, 16-19, 17-24, 17-23, 17-22, 17-21, 17-20, 17-19, 18-24, 18-23, 18-22, 18-21, 18-20, 19-24, 19-23, 19-22 or 19-21 of Hbnp. An example of an antibody that specifically binds to epitopes having an amino acid sequence containing at least three (3) amino acids of amino acids 13-20 of Hbnp is a monoclonal antibody produced by hybridoma cell line 3-631-436. The antibody can be labeled with any detectable label known to those skilled in the art, including those detectable labels discussed above in connection with the sandwich assay format.

The Hbnp peptide, Hbnp fragment or Hbnp analogue can be bound to a solid support, such as the solid supports discussed above in connection with the sandwich assay format. Preferably, the Hbnp peptide fragment has an amino acid sequence that contains amino acids 13-20, 13-19, 13-18, 13-17, 13-16, 14-20, 14-20, 14-19, 14-18, 14-17, 14-16, 15-20, 15-19, 15-18, 16-20 or 16-19 or 17-24, 17-23, 17-22, 17-21, 17-20, 17-19, 18-24, 18-23, 18-22, 18-21, 18-20, 19-24, 19-23, 19-22 or 19-21 of Hbnp.

The immobilized Hbnp peptide, Hbnp peptide fragment or Hbnp analogue thereof, test sample and at least one labeled antibody are incubated under conditions similar to those described above in connection with the sandwich assay format. Two different species Hbnp-antibody complexes are then generated. Specifically, one of the Hbnp-antibody complexes generated is immobilized and contains a detectable label while the other Hbnp-antibody complex is not immobilized and contains a detectable label. The non-immobilized Hbnp-antibody complex and the remainder of the test sample are removed from the presence of the immobilized Hbnp-antibody complex through techniques known in the art, such as washing. Once the non-immobilized Hbnp antibody complex is removed, the amount of detectable label in the immobilized Hbnp-antibody complex is then quantified. The concentration of Hbnp or Hbnp fragment in the test sample can then be determined by comparing the quantity of detectable label in the Hbnp-complex to a standard curve. The standard curve can be generated using serial dilutions of Hbnp or Hbnp fragment of known concentration, by mass spectroscopy, gravimetrically and by other techniques known in the art.

In a fluorescence polarization assay, in one embodiment, an antibody or functionally active fragment thereof is first contacted with an unlabeled test sample suspected of containing Hbnp or a Hbnp fragment thereof to form an unlabeled Hbnp-antibody complex. The unlabeled Hbnp-antibody complex is then contacted with a fluorescently labeled Hbnp, Hbnp fragment or Hbnp analogue thereof. The labeled Hbnp, Hbnp fragment or Hbnp analogue competes with any unlabeled Hbnp or Hbnp fragment in the test sample for binding to the antibody or functionally active fragment thereof. The amount of labeled Hbnp-antibody complex formed is determined and the amount of Hbnp in the test sample determined via use of a standard curve.

Preferably, the antibody used in a fluorescence polarization assay specifically binds to an epitope having an amino acid sequence comprising at least three (3) amino acids of amino acids 13-20 or 17-24 of Hbnp or to an epitope having an amino acid sequence containing (meaning including and between) amino acids 13-20, 13-19, 13-18, 13-17, 13-16, 14-20, 14-19, 14-18, 14-17, 14-16, 15-20, 15-19, 15-18, 16-20, 16-19, 17-24, 17-23, 17-22, 17-21, 17-20, 17-19, 18-24, 18-23, 18-22, 18-21, 18-20, 19-24, 19-23, 19-22 or 19-21 of Hbnp. An example of an antibody that specifically binds to epitopes having an amino acid sequence containing at least three (3) amino acids of amino acids 13-20 of Hbnp is a monoclonal antibody produced by hybridoma cell line 3-631-436.

Preferably, the Hbnp peptide fragment has an amino acid sequence that contains amino acids 13-20, 13-19, 13-18, 13-17, 13-16, 14-20, 14-20, 14-19, 14-18, 14-17, 14-16, 15-20, 15-19, 15-18, 16-20 or 16-19 or 17-24, 17-23, 17-22, 17-21, 17-20, 17-19, 18-24, 18-23, 18-22, 18-21, 18-20, 19-24, 19-23, 19-22 or 19-21 of Hbnp. The antibody, labeled Hbnp peptide, Hbnp peptide fragment or Hbnp analogue thereof and test sample and at least one labeled antibody are incubated under conditions similar to those described above in connection with the sandwich assay format.

Alternatively, in another embodiment, an antibody or functionally active fragment thereof is simultaneously contacted with a fluorescently labeled Hbnp, Hbnp fragment or Hbnp analogue thereof and an unlabeled test sample suspected of containing Hbnp or a Hbnp fragment thereof to form both labeled Hbnp-antibody complexes and unlabeled Hbnp-antibody complexes. The amount of labeled Hbnp-antibody complex formed is determined and the amount of Hbnp in the test sample determined via use of a standard curve. The antibody used in this immunoassay specifically binds to an epitope having an amino acid sequence comprising at least three (3) amino acids of amino acids 13-20 or 17-24 of Hbnp or to an epitope having an amino acid sequence containing (meaning including and between) amino acids 13-20, 13-19, 13-18, 13-17, 13-16, 14-20, 14-19, 14-18, 14-17, 14-16, 15-20, 15-19, 15-18, 16-20, 16-19, 17-24, 17-23, 17-22, 17-21, 17-20, 17-19, 18-24, 18-23, 18-22, 18-21, 18-20, 19-24, 19-23, 19-22 or 19-21 of Hbnp. An example of an antibody that specifically binds to epitopes having an amino acid sequence containing at least three (3) amino acids of amino acids 13-20 of Hbnp is a monoclonal antibody produced by hybridoma cell line 3-631-436. Additionally, the Hbnp peptide fragment has an amino acid sequence that contains amino acids 13-20, 13-19, 13-18, 13-17, 13-16, 14-20, 14-20, 14-19, 14-18, 14-17, 14-16, 15-20, 15-19, 15-18, 16-20 or 16-19 or 17-24, 17-23, 17-22, 17-21, 17-20, 17-19, 18-24, 18-23, 18-22, 18-21, 18-20, 19-24, 19-23, 19-22 or 19-21 of Hbnp.

Alternatively, in yet another embodiment, an antibody (such as a monoclonal antibody produced by hybridoma cell line 3-631-436) or functionally active fragment thereof is first contacted with a fluorescently labeled Hbnp, Hbnp fragment or Hbnp analogue thereof to form a labeled Hbnp-antibody complex. The labeled BNP-antibody complex is then contacted with an unlabeled test sample suspected of containing Hbnp or a Hbnp fragment thereof. Any unlabeled Hbnp or Hbnp fragment in the test sample competes with the labeled Hbnp, Hbnp fragment or Hbnp analogue for binding to the antibody or functionally active fragment thereof. The amount of labeled Hbnp-antibody complex formed is determined the amount of Hbnp in the test sample determined via use of a standard curve. The antibody used in this immunoassay specifically binds to an epitope having an amino acid sequence comprising at least three (3) amino acids of amino acids 13-20 or 17-24 of Hbnp or to an epitope having an amino acid sequence containing (meaning including and between) amino acids 13-20, 13-19, 13-18, 13-17, 13-16, 14-20, 14-19, 14-18, 14-17, 14-16, 15-20, 15-19, 15-18, 16-20, 16-19, 17-24, 17-23, 17-22, 17-21, 17-20, 17-19, 18-24, 18-23, 18-22, 18-21, 18-20, 19-24, 19-23, 19-22 or 19-21 of Hbnp. An example of an antibody that specifically binds to epitopes having an amino acid sequence containing at least three (3) amino acids of amino acids 13-20 of Hbnp is a monoclonal antibody produced by hybridoma cell line 3-631-436. Additionally, the Hbnp peptide fragment has an amino acid sequence that contains amino acids 13-20, 13-19, 13-18, 13-17, 13-16, 14-20, 14-20, 14-19, 14-18, 14-17, 14-16, 15-20, 15-19, 15-18, 16-20 or 16-19 or 17-24, 17-23, 17-22, 17-21, 17-20, 17-19, 18-24, 18-23, 18-22, 18-21, 18-20, 19-24, 19-23, 19-22 or 19-21 of Hbnp.

By way of example and not of limitation, examples of the present invention shall now be given.

Example 1

Immunogen Preparation

The antigen used to stimulate the immune response in the mice was synthetic, cyclized Hbnp (containing amino acids 1-32) which is available from Peptide Institute, Inc., Osaka, Japan. This cyclized Hbnp has the amino acid sequence shown below:

```
                                          (SEQ ID NO: 1)
NH2-SPKMVQGSGCFGRKMDRISSSSGLGCKVLRRH-COOH
    (Disulfide bond between C¹⁰-C²⁶)
```

Alternately, a modified BNP molecule could be used as an immunogen to produce a monoclonal or polyclonal antibody reactive to Hbnp. One such immunogen replaces one of the amino acids in the epitope included within amino acids 13 to 20 with a different amino acid. For example, the lysine at position 14 in SEQ ID NO:1, the methionine at position 15 in SEQ ID NO:1 or the serine at position 19 in SEQ ID NO:1 could all or each be replaced with a different amino acid, such as, but not limited to, an alanine.

Example 2

Immunizations

The mouse model used was a female RBf/Dnj from Jax Labs, Harbor, Me., aged between 5-6 weeks old. The animal was immunized with Hbnp (SEQ ID NO:1 from Example 1 above) 6 times over 12 weeks using alternating Freunds Adjuvant (DIFCO, Detroit, Mich.) and RIBI Adjuvant (Corixa, Hamilton, Mont.) in 5-10 ug boosts. Two weeks after the 6$^{th}$ boost, the sera sample was tested on a microtiter EIA. Rabbit anti-mouse Fc Ig (RAMFc) (Jackson ImmunoResearch, West Grove, Pa.) diluted in saline was coated at 0.1 ug/well, incubated, then blocked with 2% fish gelatin. The plate was washed and serially diluted mouse sera samples were added for an 1 hour incubation. BNP peptide, containing amino acids 1-32 (SEQ ID NO:1), was diluted in Normal Mouse Serum (Fitzgerald Industries International, Concord, Mass.) and added to the wells. Following an incubation and wash, the detector reagent, monoclonal antibody (hereinafter "mAb") 106.3 conjugated to alkaline phosphatase (hereinafter referred to as "106-Alkaline Phosphatase") was added to each well. Color development was achieved with the p-NPP substrate system (KPL, Gaithersburg, Md.) and two mice, #1494 and 1499, with titers>1/10,000 were selected for fusion. The animals were then rested for one additional week prior to ☐dministering 10 ug Hbnp (SEQ ID NO:1) in saline intrasplenic pre-fusion boost.

Example 3

Spleen Cell Fusions

Three days after the pre-fusion boost, the splenic B-cells from the mice in Example 2 were used in a PEG-mediated fusion with the SP2/0 myeloma cell line. The cells were resuspended in serum free medium then pelleted by centrifugation. The supernate was discarded. Polyethylene glycol having a molecular weight (MW) of 1450 (ATCC, Manassas, Va.) was exposed to the cells by slowly adding 1 ml over 15-30 seconds followed by a 1 minute incubation, then washed in serum free medium. The cells were resuspended in HAT supplemented H-SFM (Life Technologies, Grand Island, N.Y.) with 10% FBS (Hyclone, Logan, Utah) and plated at a concentration of 1-5×10$^5$ cells/well. The plates were incubated for 10 days at 37° C. prior to screening using the microtiter EIA previously described in Example 2.

Example 4

Screening and Selection

The plates were incubated for 10 days in a 37° C. prior to screening using the microtiter sandwich EIA previously described in Example 2. Positive cultures were expanded and frozen. Saturated supernates were then collected and retested for reactivity to the Hbnp peptide fragment containing amino acids 1-26 (SEQ ID NO:2), a "lollipop-like" modification of the Hbnp peptide (see Table 1, below) thereby avoiding mAbs reactive to the Hbnp C-terminal region comprising amino acids 27-32 (SEQ ID NO:6). Microwell plates were coated with 0.1 ug/well RAMFc, then blocked with fish gelatin. The plates were washed and serially diluted and supernates added. Next, the Hbnp peptide fragment containing amino acids 1-26 was conjugated to biotin (SEQ ID NO:3) (Abbott Laboratories, GPRD, Abbott Park, Ill.; see Table 1, below) were added to the wells, incubated and washed. The signal detector, strepavidin-HRPO conjugate (Zymed, San Francisco, Calif.) was added at a 1/5000 dilution in block, incubated, washed and followed by the OPD substrate system (Abbott Laboratories, Abbott Park, Ill.) for color development. The hybrid 3-631 scored reactive to biotinylated Hbnp peptide fragment containing amino acids 1-26 in this assay configuration and was selected for further testing. (See FIG. 1).

Figure 2:
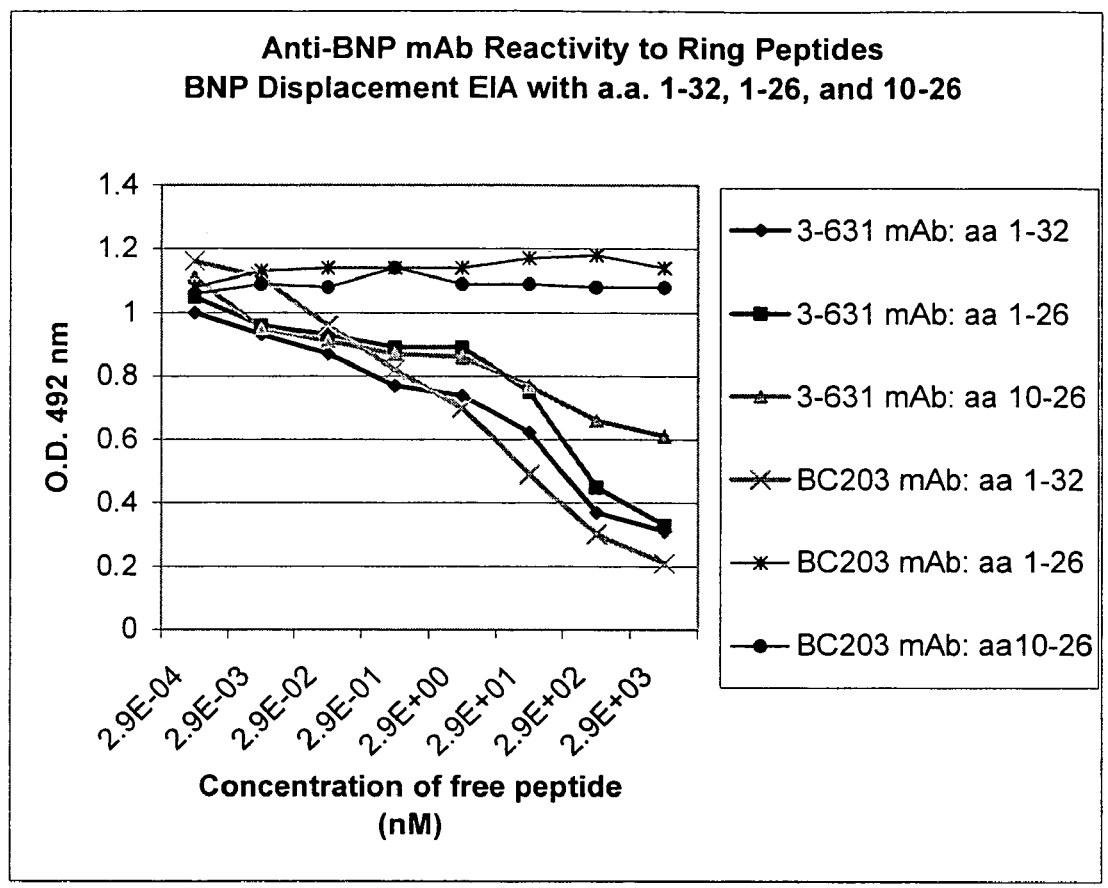
FIG. 2 is a graph showing the results of a displacement EIA conducted using full length cyclic Hbnp (amino acids 1-32) as well as a number of Hbnp ring peptide fragments and a monoclonal antibody produced from hybridoma cell line 3-631-435 and a monoclonal antibody produced from hybridoma cell line BC203.

Next, the hybrid 3-631 mAb was tested in a displacement EIA using a series of unlabeled cyclized ring Hbnp peptides. The Hbnp peptide (amino acids 1-32) (SEQ ID NO:1), Hbnp peptide fragments containing amino acids 1-26 (SEQ ID NO:2) (Abbott Laboratories, GPRD, Abbott Park, Ill.; see Table 1, below) and modified Hbnp fragments containing amino acids 10-26 (SEQ ID NO:4) (Abbott Laboratories, GPRD, Abbott Park, Ill.; see Table 1, below) were used to compete for binding to the 3-631 mAb against a biotinylated Hbnp peptide (amino acids 1-32) (SEQ ID NO:5). (see Table 1, below) A RAMFc coated microtiter plate was incubated overnight, washed and blocked with 2% fish gelatin. Titered test antibody was allowed to react for one hour and plates were washed prior to adding serially diluted members of the modified peptide panel and control Hbnp peptide (amino acids 1-32) (SEQ ID NO:1) at concentrations ranging from 0.00029-2900.0 Nm free peptide. The plates were washed once again and the biotinylated Hbnp conjugate was then added and allowed to compete with the unlabeled peptides for binding to the bound 3-631 antibody. The control Hbnp cyclized peptide (amino acids 1-32) successfully blocked the biotinylated 1-32 signal for binding to the 3-631 antibody as did the modified Hbnp peptide fragments containing amino acids 1-26 (See SEQ ID NO:2) and 10-26 (See SEQ ID NO:4), respectively. (See FIG. 2)

Hybrid 3-631 was cloned by limiting dilution and incubated at 37° C. until confluent growth was apparent. Clone supernates were tested in the EIA described above in Example 2 with the exception of using Hbnp peptide (amino acids 1-32) conjugated to biotin (see Table 1, below). The subsequent cell line identified, 3-631-264, was weaned to a serum free medium, H-SFM (Life Technologies). The cell line was subcloned once again, this time using the FACSAria flow cytometer to isolate a single cell stained with Goat anti-mouse Ig conjugated to Alexa-633 (Molecular Probes). The cultures were incubated for 10-14 days and screened using the previously described microtiter EIA (see Example 2) with the Hbnp peptide (amino acids 1-32) conjugated to biotin (See Table 1, below). Cell line 3-631-436 was selected for scale up and cell banking purposes. The cell bank was stored long term in liquid nitrogen freezers.

TABLE 1

1. Modified cyclic BNP amino acid 1-26 "lollipop-like" configuration
   NH2-SPKMVQGSGCFGRKMDRISSSSGLGC (SEQ ID NO:2)
   (Disulfide bond between $C^{10}$-$C^{26}$)

2. Biotinylated, modified cyclic BNP amino acid 1-26 "lollipop" configuration
   biotin-SPKMVQGSGCFGRKMDRISSSSGLGC (SEQ ID NO:3)
   (Disulfide bond between $C^{10}$-$C^{26}$)

3. Modified cyclic BNP amino acid 10-26 "lifesaver-like" configuration
   CFGRKMDRISSSSGLGC (SEQ ID NO:4)
   (Disulfide bond between $C^{1}$-$C^{17}$)

4. Biotinylated cyclic BNP amino acid 1-32
   biotin-SPKMVQGSGCFGRKMDRISSSSGLGCKVLRRH-COOH (SEQ ID NO:5)
   (Disulfide bond between $C^{10}$-$C^{26}$)

5. C-terminus of cyclic BNP amino acids 27-32
   KVLRRH-COOH (SEQ ID NO:6)

6. Cyclic ANP-28 amino acids
   SLRRSSCFGGRMDRIGAQSGLGCNSFRY (SEQ ID NO:7)
   (Disulfide bond between $C^{7}$-$C^{23}$)

7. Cyclic CNP-22 amino acids
   GLSKGCFGLKLDRIGSMSGLGC (SEQ ID NO: 8)
   (Disulfide bond between $C^{6}$-$C^{22}$)

Example 5

Characterization of Antibodies

Isotype Determination

Purified antibody from the 3-631-436 cell line was tested with the Isostrip Mouse Monoclonal Antibody Isotyping Kit, (Roche Diagnostics). An aliquot of 150 ul of a 0.3 ug/ml sample was added to the development tube and mixed. The Isostrip was added to the tube and incubated for 5-10 minutes until color developed on the strip's band. The results indicated that the 3-631-436 mAb is mouse IgG2a subtype with a kappa light chain.

Electrophoretic Evaluation

The purified antibody was evaluated on SDS-PAGE and IEF gels using the PhastSystem (Amersham/Pharmacia) according to manufacturer's instructions. DTT treated test samples were loaded onto the lanes of the SDS-Page gel at concentrations from 0.1 to 0.4 mg/ml. Color development with silver stain indicated that the light chain molecular weight (MW) was ~21 kDa and the heavy chain MW was ~46 kDa. The IEF test samples were loaded into the lanes with 0.15-0.6 mg/ml. Color development of the IEF test run indicated the Pi range was 6.0-6.8 with 9 visible bands.

Affinity Determination

The affinity binding rates and binding constants for the interaction of 3-631-436 mAb and Hbnp antigen were evaluated on the Biacore (Biacore, Inc., Sweden). A GAMFc (KPL, Gaithersburg, Md.) coated chip was used to capture the purified 3-631-436 or 106.3 antibody. Next, free Hbnp peptide (amino acids 1-32) (SEQ ID NO:1) was allowed to interact with each mAb and the data was collected for analysis. See Table 2, below.

TABLE 2

|  | Kon (1/Ms) | Koff (1/s) | KA (1/M) | KD (M) |
| --- | --- | --- | --- | --- |
| 3-631-436 mAb | $6.99 \times 10^6$ | $1.79 \times 10^{-3}$ | $3.89 \times 10^9$ | $2.57 \times 10^{-10}$ |
| 106.3 mAb | $1.57 \times 10^7$ | $1.83 \times 10^{-4}$ | $8.59 \times 10^{10}$ | $1.16 \times 10^{-11}$ |

In addition, the affinity binding rates and binding constants of the 3-631-436 mAb binding to the modified cyclic Hbnp fragment containing amino acids 1-26 (SEQ ID NO:2) were determined in the Biacore assay described above. See Table 3, below.

TABLE 3

|  | Kon (1/Ms) | Koff (1/s) | KA (1/M) | KD (M) |
| --- | --- | --- | --- | --- |
| 3-631-436 mAb | $2.43 \times 10^6$ | $1.5 \times 10^{-3}$ | $1.62 \times 10^9$ | $6.16 \times 10^{-10}$ |
| 106.3 mAb | $5.79 \times 10^6$ | $3.61 \times 10^{-4}$ | $1.6 \times 10^{10}$ | $6.24 \times 10^{-11}$ |

Cross Reactivity

Figure 3:
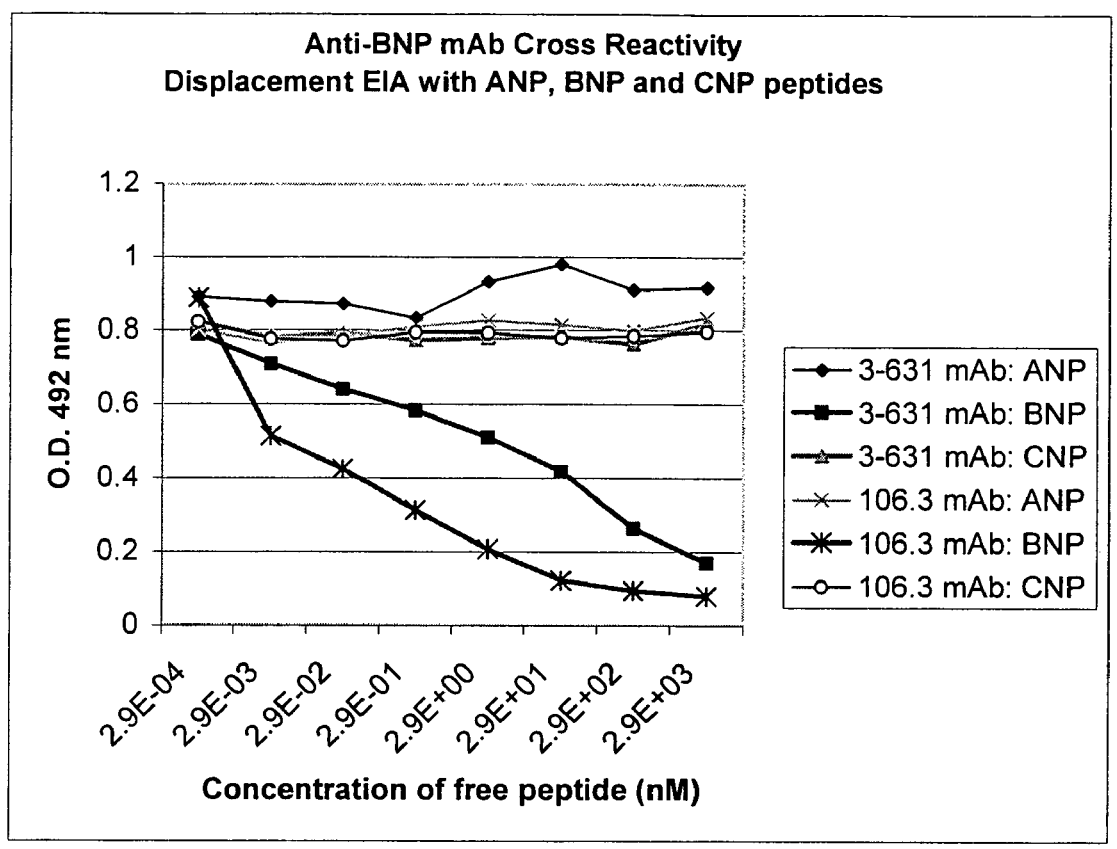
FIG. 3 is a graph showing the results of a displacement EIA conducted using full length cyclic Hbnp (amino acids 1-32), full length cyclic ANP (amino acids 1-28), and the 22 amino acid form of cyclic CNP and a monoclonal antibody produced from hybridoma cell line 3-631-435 and a monoclonal antibody produced from hybridoma cell line 106.3.

The 3-631-436 mAb reactivity to ANP and CNP was determined in a displacement microtiter EIA. Blocked RAMFc coated plates were incubated with mAb for 1 hour and washed. Serially diluted free, unconjugated ANP (SEQ ID NO:7) (Peptide Institute, Inc. Osaka, Japan) and CNP (SEQ ID NO:8) (Peptide Institute, Inc.) were allowed to react with the mAb for one hour prior to washing then adding the biotinylated Hbnp conjugate (SEQ ID NO:3). The plates were incubated, washed and the detector reagent, streptavidin-HRPO, was added. Following color development, the data analysis did not reveal cross reactivity of the 3-631-436 mAb to ANP and CNP. (See FIG. 3).

Additional Testing

The purified 3-631-436 antibody was tested to determine the antibody's ability to bind to the linear form of the Hbnp. The Hbnp peptide (amino acids 1-32) (SEQ ID NO:1) was prepared without the peptide cyclization process whereby the two internal cysteines did not form the disulfide bond to create the typical Hbnp ring. These linear Hbnp reagents were prepared by Abbott Laboratories, Abbott Park, Ill., and mimic a cyclic Hbnp peptide that has been treated under reducing conditions that break a disulfide bond. Using the Biacore assay described above, it was determined that the 3-631-436 mAb can bind to the linear peptide. See Table 4, below.

TABLE 4

| | Kon (1/Ms) | Koff (1/s) | KA (1/M) | KD (M) |
|---|---|---|---|---|
| 3-631-436 mAb | $2.5 \times 10^3$ | $6.6 \times 10^{-4}$ | $3.98 \times 10^6$ | $2.51 \times 10^{-7}$ |
| 106.3 mAb | $3.06 \times 10^3$ | $1.13 \times 10^{-5}$ | $1.13 \times 10^8$ | $8.83 \times 10^{-9}$ |

Figure 4:
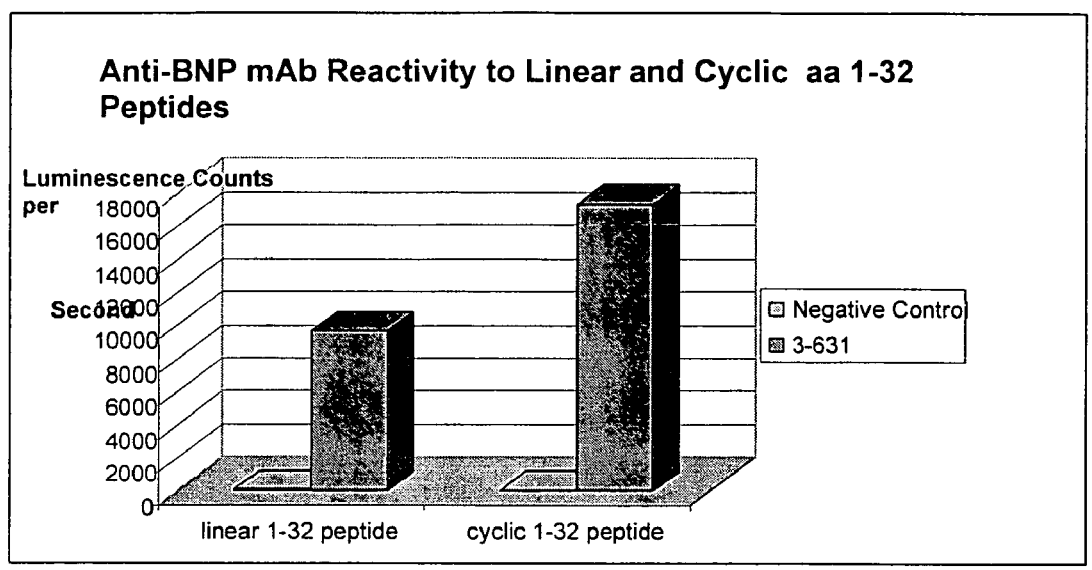
FIG. 4 is a graph showing the results of an assay to determine anti-BNP reactivity to linear and cyclic BNP (amino acids 1-32).

A chemiluminescent assay was also developed to determine the binding capacity of 3-631-436 to the linear form of the Hbnp to present the molecule in a condition similar to reducing conditions. A sandwich assay with the 3-631-436 antibody bound to the solid phase was used to capture either the linear and cyclic forms of Hbnp at a concentration of 0 and 10,000 pg/ml. The 106.3 mAb, conjugated to acridinium, was then added to the sample wells. The chemiluminescent signal was triggered and read on a Wallac chemiluminescent reader (See FIG. 4).

Example 6

Antibody Production and Purification

The 3-631-436 cell line was expanded in serum free medium and seeded into roller bottles at approximately 0.4×$10^5$ cells/ml. The culture was incubated at 1 revolution per minute for 10-14 days or until a terminal end culture was obtained. The supernate was harvested and filtered with a 0.45 μm filter. The supernate was concentrated using a Pellicon system and filtered with a 0.45 μm filter. The mAb concentrate was diluted 1:1 with a 1.5 M glycine/3 M NaCl buffer, Ph 8.9, and loaded onto a pre-equilibrated 5 ml Protein A column using the AKTA automated purification system (Amersham/Pharmacia). The column was then washed with the 5× binding buffer and when baseline was achieved, the mAb is eluted with a Ph 3.0 citrate buffer. The mAb was then transferred to a 70 ml G25 column for a buffer exchange into PBS. The antibody was aliquoted and stored at −70° C.

Example 7

Epitope Analysis

The binding site of the 3-631-436 mAb was identified using an alanine mutagenesis screening procedure with the cyclic Hbnp alanine-substituted peptide panel. Single amino acids of the Hbnp peptide (amino acids 1-32) (SEQ ID NO:1) were replaced with an alanine amino acid to form a 28-member panel as shown in Table 5 below (SEQ ID NO:9 through SEQ ID NO:36). A high density Goat anti-mouse Fc (GAMFc) antibody surface plasma resonance (SPR) biosensor was prepared by immobilizing GAMFc onto a carboxymethyl-dextran biosensor (BIAcore CM5 Chip) by amine coupling. ~10 Kru of GAMFc is coupled to the biosensor. Antibody and each Hbnp peptide were diluted to their testing concentrations (10 μg/Ml and 20 to 20,000 Nm, respectfully) into degassed/vacuum-filtered running buffer composed of HBS-EP (BIAcore) with 12 mg/Ml BSA and 12 mg/Ml carboxymethyl dextran sodium salt. 60 μL of anti-BNP mAbs (3-631-436 and 106.3) and a non-specific, reference mAb were flowed at 10 μL/min through different flow cells so that each flow cell contains ~0.8 to 1.2 Kru of captured mAb. The chip was allowed to equilibrate for 10 minutes with running buffer at a flow rate of 100 μL/min before 150 μL peptide and then buffer were injected serially over the capture mAb surfaces using KINJECT (90 s association, 300 s dissociation) on the BIAcore 2000. The surface is then regenerated with three 35 second pulses of 10 Mm glycine, Ph 1.8 at a flow rate of 100 μL/min at 25° C.

Figure 5A:
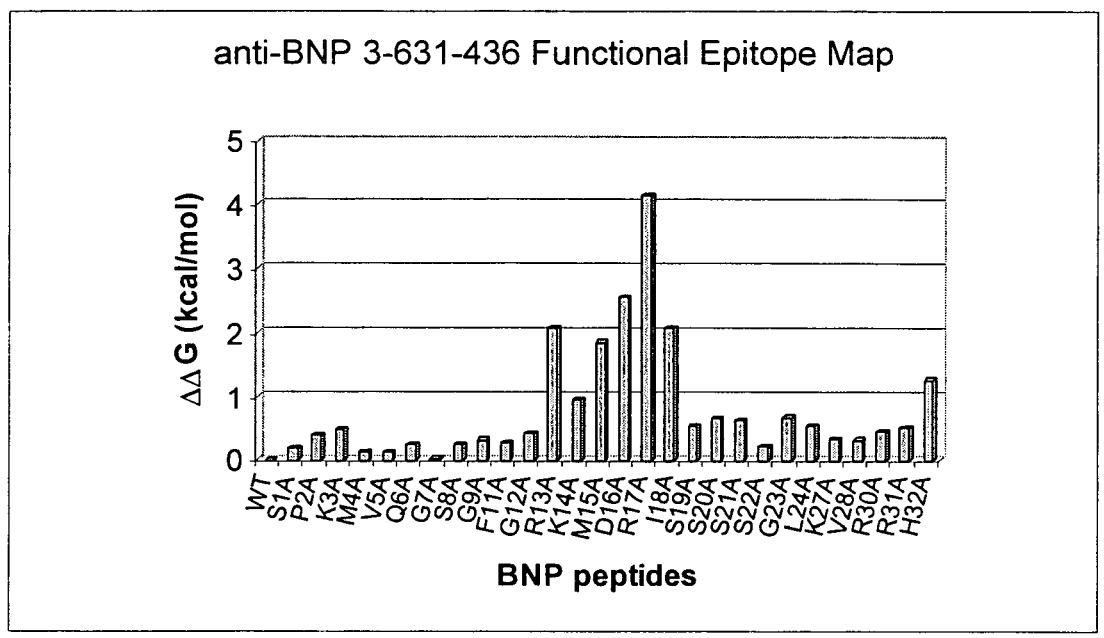
FIG. 5a is a graph showing the results of Biacore functional epitope mapping using a mutagenesis panel of cyclic Hbnp peptides with alanine substitutions and monoclonal antibody produced from hybridoma cell line 3-631-435.
Figure 5B:
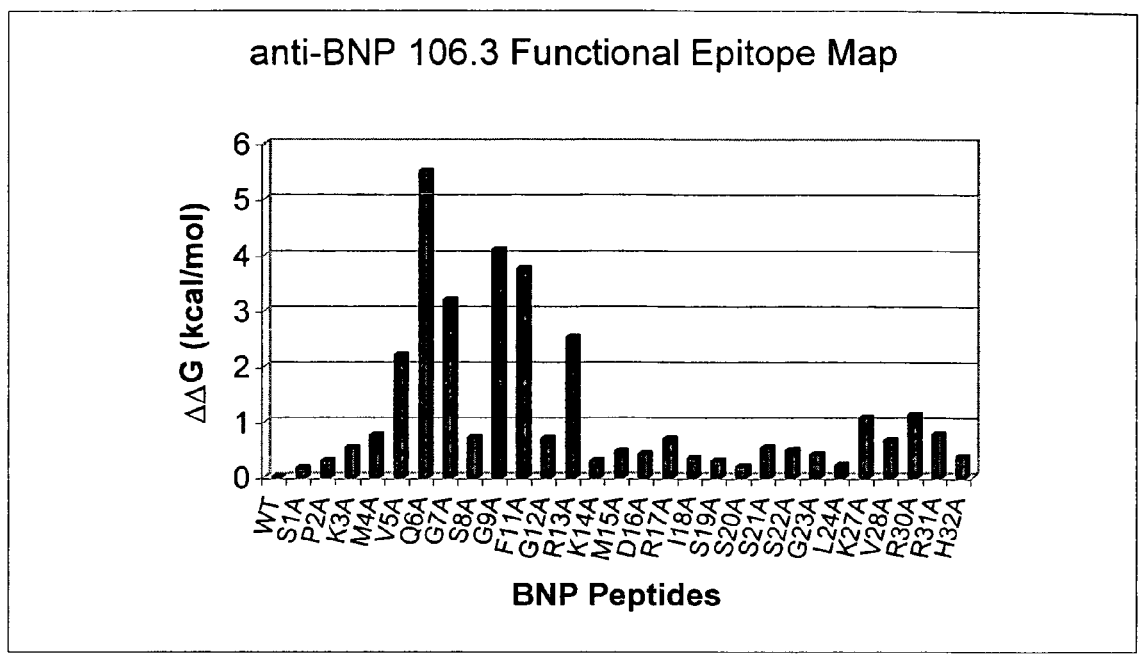
FIG. 5b is a graph showing the results of the Biacore functional epitope mapping using a panel of cyclic Hbnp peptides with alanine substitutions and a monoclonal antibody produced from hybridoma cell line 106.3.

The dissociation constants (KD) were determined for each peptide and directly calculated into free energy (ΔG). The energy difference between the wild-type (WT) and the mutants were calculated (ΔΔG) and plotted. ΔΔG values of 1.5-2.0 kcal/mol or greater are considered hot spots for binding and are part of the functional binding epitope (Bogan & Thorn., *JMB,* 280:1-9 (1998) and Ma, Elkayam, Wolfson, and Nussinov, *PNAS USA,* 100: 5772-7 (2003)). The residues on Hbnp that are functionally important for binding with anti-BNP-3-631-436 are R13, D16, R17, and I18. These amino acids form Hbnp's functional binding epitope with anti-BNP 3-631-436. The residues on Hbnp that are functionally important for binding with anti-BNP 106.3 are V5, Q6, G7, G9, F11, and R13. These amino acids form Hbnp's functional binding epitope with anti-BNP 106.3. See FIGS. 5*a* and 5*b*.

3-631-436 mAb functional epitope (shown in bold and underlined):

(SEQ ID NO: 1)

NH2-SPKMVQGSGCFGRKMDRISSSSGLGCKVLRRH-COOH 106.3 mAb functional epitope (shown in bold and underlined):

(SEQ ID NO: 1)

NH2-SPKMVQGSGCFGRKMDRISSSSGLGCKVLRRH-COOH

TABLE 5

| di-sulfide bonds: 10 = 26 | | |
|---|---|---|
| BNP S1A: | APKMVQGSGCFGRKMDRISSSSGLGCKVLRRH-OH | (SEQ ID NO:9) |
| BNP P2A: | SAKMVQGSGCFGRKMDRISSSSGLGCKVLRRH-OH | (SEQ ID NO:10) |
| BNP K3A: | SPAMVQGSGCFGRKMDRISSSSGLGCKVLRRH-OH | (SEQ ID NO:11) |
| BNP M4A: | SPKAVQGSGCFGRKMDRISSSSGLGCKVLRRH-OH | (SEQ ID NO:12) |
| BNP V5A: | SPKMAQGSGCFGRKMDRISSSSGLGCKVLRRH-OH | (SEQ ID NO:13) |
| BNP Q6A: | SPKMVAGSGCFGRKMDRISSSSGLGCKVLRRH-OH | (SEQ ID NO:14) |
| BNP G7A: | SPKMVQASGCFGRKMDRISSSSGLGCKVLRRH-OH | (SEQ ID NO:15) |
| BNP S8A: | SPKMVQGAGCFGRKMDRISSSSGLGCKVLRRH-OH | (SEQ ID NO:16) |
| BNP G9A: | SPKMVQGSACFGRKMDRISSSSGLGCKVLRRH-OH | (SEQ ID NO:17) |

TABLE 5-continued di-sulfide bonds: 10 = 26

BNP F11A: SPKMVQGSGCAGRKMDRISSSSGLGCKVLRRH-OH (SEQ ID NO:18)

BNP G12A: SPKMVQGSGCFARKMDRISSSSGLGCKVLRRH-OH (SEQ ID NO:19)

BNP R13A: SPKMVQGSGCFGAKMDRISSSSGLGCKVLRRH-OH (SEQ ID NO:20)

BNP K14A: SPKMVQGSGCFGRAMDRISSSSGLGCKVLRRH-OH (SEQ ID NO:21)

BNP M15A: SPKMVQGSGCFGRKADRISSSSGLGCKVLRRH-OH (SEQ ID NO:22)

BNP D16A: SPKMVQGSGCFGRKMARISSSSGLGCKVLRRH-OH (SEQ ID NO:23)

BNP R17A: SPKMVQGSGCFGRKMDAISSSSGLGCKVLRRH-OH (SEQ ID NO:24)

BNP I18A: SPKMVQGSGCFGRKMDRASSSSGLGCKVLRRH-OH (SEQ ID NO:25)

BNP S19A: SPKMVQGSGCFGRKMDRIASSSGLGCKVLRRH-OH (SEQ ID NO:26)

BNP S20A: SPKMVQGSGCFGRKMDRISASSGLGCKVLRRH-OH (SEQ ID NO:27)

BNP S21A: SPKMVQGSGCFGRKMDRISSASGLGCKVLRRH-OH (SEQ ID NO:28)

BNP S22A: SPKMVQGSGCFGRKMDRISSSAGLGCKVLRRH-OH (SEQ ID NO:29)

BNP G23A: SPKMVQGSGCFGRKMDRISSSSALGCKVLRRH-OH (SEQ ID NO:30)

BNP L24A: SPKMVQGSGCFGRKMDRISSSSGAGCKVLRRH-OH (SEQ ID NO:31)

BNP K27A: SPKMVQGSGCFGRKMDRISSSSGLGCAVLRRH-OH (SEQ ID NO:32)

BNP V28A: SPKMVQGSGCFGRKMDRISSSSGLGCKALRRH-OH (SEQ ID NO:33)

BNP R30A: SPKMVQGSGCFGRKMDRISSSSGLGCKVLARH-OH (SEQ ID NO:34)

BNP R31A: SPKMVQGSGCFGRKMDRISSSSGLGCKVLRAH-OH (SEQ ID NO:35)

BNP H32A: SPKMVQGSGCFGRKMDRISSSSGLGCKVLRRA-OH (SEQ ID NO:36)

di-sulfide bond

Example 8

Sandwich Assay Using Monoclonal Antibody Produced by Hybridoma Cell Lines 3-631-435

For the ARCHITECT®-Hbnp assay (hereinafter referred to as "Arc-BNP") paramagnetic particles were coated with mAb 106.3 (SEQ ID NO:6). This mAb binds to an amino acid sequence containing amino acids 5-13 on the Hbnp peptide. Monoclonal antibody 106.3 is described in U.S. Pat. No. 6,162,902. Monoclonal antibody 106.3 was coated onto a paramagnetic particle (Polymer Laboratories, Amherst, Mass.) using the techniques described in U.S. Pat. No. 6,162,902. Specifically, EDAC coupling was used (EDAC is generally used as a carboxyl activating agent for amide bonding with primary amines. In addition, it reacts with phosphate groups. It is used in peptide synthesis, crosslinking proteins to nucleic acids and in preparing immunoconjugates. The chemical formula for EDAC is 1-ethyl-3-(3-dimethylaminopropyl)carbodiimide, hydrochloride. EDAC is commercially available from Sigma-Aldrich, St. Louis, Mo.). Particles were washed and overcoated with BSA. These particles were used to capture BNP peptide in the assay during the first ($1^{st}$) incubation with specimens.

Monoclonal antibody BC203 was conjugated to acridinium (Albany Molecular Research Inc., Albany, N.Y.) and is used in the assay during the second (2.sup.nd) incubation to detect the particle-bound Hbnp peptide. The conjugation occurred by reaction of BC203 to an acridinium-carboxamide ester. Monoclonal antibody BC203 binds to an epitope having the amino acid sequence of LYS-VAL-LEU-ARG-ARG-HIS (SEQ ID NO:6) that is found in the C-terminal region of Hbnp, namely epitopes 27-32. Monoclonal antibody BC203 is commercially available from Shionogi & Co., Ltd. (Osaka, Japan) and is described in U.S. Pat. No. 6,677,124.

For the modified Arc-BNP assay, paramagnetic particles were coated with mAb 3-631-436. These are used to capture Hbnp peptide in the assay during the first ($1^{st}$) incubation with specimens. Monoclonal antibody 106.3 was conjugated to acridinium the same way Mab BC203 was conjugated to the acridinium and is used in the assay during the $2^{nd}$ incubation to detect the particle-bound Hbnp peptide.

The degraded plasma was assayed on both ARCHITECT® formats and Hbnp concentrations were plotted as a function of timepoint. To test for improved detection of degraded samples, a panel was made as follows. An EDTA-plasma (pooled from normal healthy individuals) was spiked with Hbnp peptide (amino acids 1-32) (Peptide International, Louisville, Ky.) and was allowed to sit at room temperature for up to 24 hours to degrade the Hbnp peptide. Protease inhibitors were added to aliquots of the spiked pool at certain time points (0, 4, 6, 8, 10, 24 hours). These aliquots were taken starting at time point 0 hours, through time point 24 hours. Aliquots were placed in a −70° C. freezer at each time point. These aliquots were thawed for testing in the different assay formats.

The ARCHITECT® results with the Modified format shows a marked improvement to retaining the Hbnp signal as a function of degradation time. The original Arc-BNP format shows that the Hbnp signal is greatly depressed even after only 4 hours of degradation time. This shows that the modified Arc-BNP format is an improvement.

A BNP immunoassay was performed on an ARCHITECT® instrument (this instrument is described in U.S. Pat. No. 5,468,646).

An aliquot containing a calibrator solution or specimen was delivered to the same well of the reaction vessel as the microparticles to form a reaction mixture. The calibrator solution contained Hbnp full-length peptide. The 4.5 µm microparticles coated with the capture antibody in a diluent containing 16% sucrose, sodium azide, 100 Mm NaCl, 50 Mm Tris and 1% BSA were pipetted by the sampling probe into the appropriate wells of the reaction vessel in the sampling center. The reaction mixture was incubated for approximately 4 minutes at a temperature of about 37° C. After the incubation, the reaction mixture was washed with the ARCHITECT® Line Diluent to remove any of the calibrator or specimen that was not captured. The ARCHITECT® Line Diluent is commercially available from Abbott Laboratories, Abbott Park, Ill.

The mAb-Acridinium-conjugate at about 50-100 ng/Ml in a buffer containing BgG (Bovine Gamma Globulin), polyethylene glycol (PEG), sucrose, ProClin® 300 (Sigma-Aldrich, St. Louis, Mo., the active ingredients of ProClin® 300 are 5-chloro-2-methyl-4-isothiazolin-3-one and 2-methyl-4-isothiazolin-3-one. ProClin® 300 also contains a number of inert ingredients such as a modified glycol and alkyl carboxylate) and sodium azide, were dispensed into the reaction vessel and the resulting combination was incubated for approximately 4 minutes at a temperature of about 37° C. After the incubation, the reaction vessel was washed with the ARCHITECT® Line Diluent to remove the unbound materials.

A solution of hydrogen peroxide and then sodium hydroxide was added to the reaction vessel and the chemiluminescent signal was measured by the chemiluminescent mircoparticle immunoassay (CMIA) optical assembly of the ARCHITECT® instrument.

Figure 6:
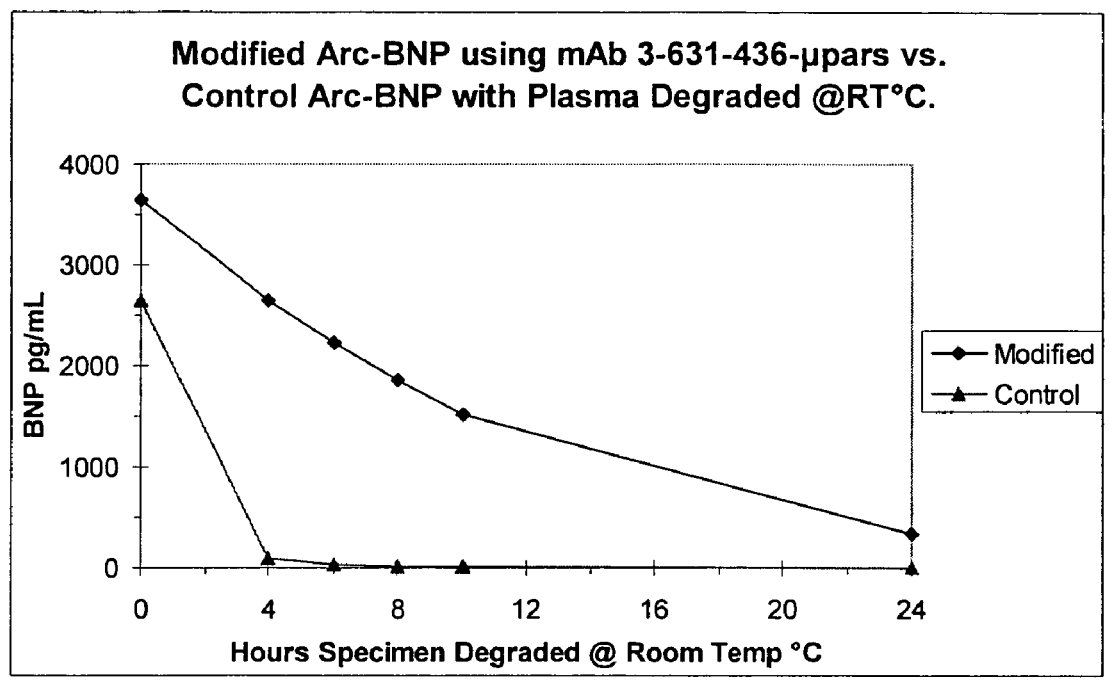
FIG. 6 shows the results of the sandwich assay described in Example 8 using a monoclonal antibody produced from hybridoma cell line 3-631-435 (referred to as "Modified Arc-BNP") versus a control (referred to as "Arc-BNP"). The results are shown in pg/Ml Hbnp of degraded plasma.
Figure 7:
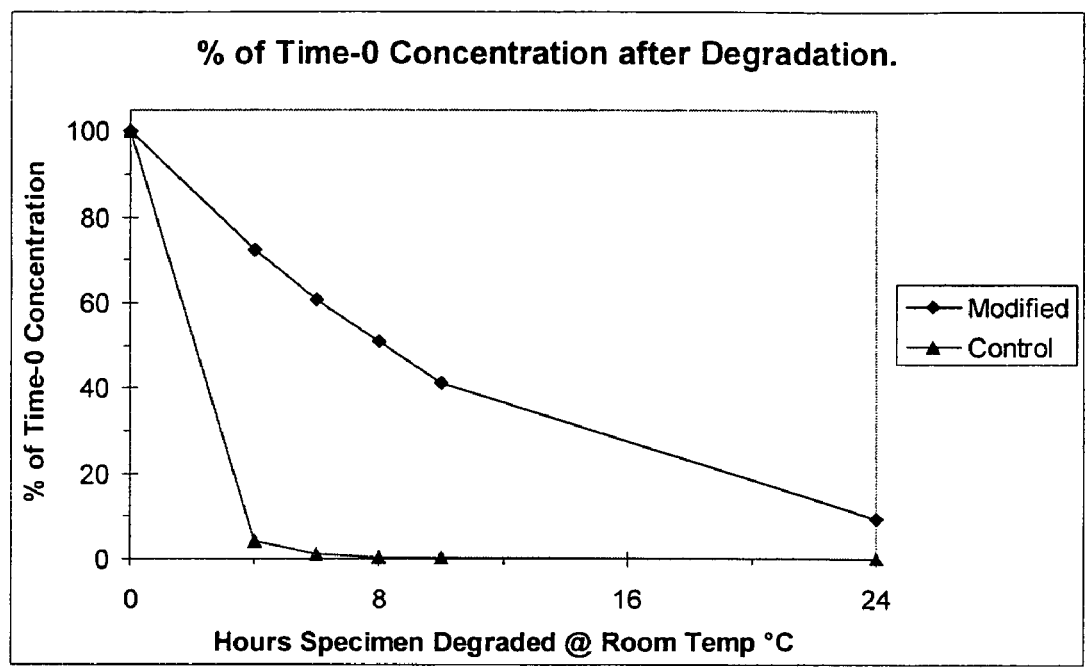
FIG. 7 shows the results of the sandwich assay of Example 8 using a monoclonal antibody produced from hybridoma cell line 3-631-435 (Modified Arc-BNP) versus a control (Arc-BNP). The results are shown in % of Time-0 Concentration After Degradation.

The ARCHITECT® system measures the acridinium signals which are typically measured in relative light units (hereinafter "rlu's"). The assay was conducted twice for each calibrator. The results in Tables 6 and 7 below and FIGS. 6 and 7 show the mean of the two assays. Specifically, the results in Table 6 and FIG. 6 are shown in pg/Ml BNP of Degraded Plasma. The results in Table 7 and FIG. 7 are shown in % Time—0 Concentration After Degradation.

TABLE 6

| pg/Ml Degraded | Time in Hours | Modified | Control | Hbnp of Plasma |
|---|---|---|---|---|
| | 0 | 3653 | 2641 | |
| | 4 | 2638 | 105 | |
| | 6 | 2220 | 34 | |
| | 8 | 1861 | 14 | |
| | 10 | 1508 | 8 | |
| | 24 | 345 | 5 | |

TABLE 7

| | | Concentration After Degradation | |
|---|---|---|---|
| % Time-0 | Time in Hours | Modified | Control |
| | 0 | 100.0 | 100.0 |
| | 4 | 72.2 | 4.0 |
| | 6 | 60.8 | 1.3 |
| | 8 | 50.9 | 0.5 |
| | 10 | 41.3 | 0.3 |
| | 24 | 9.4 | 0.2 |

Example 9

ATCC Deposit Information

Murine hybridoma cell line 3-631-436 was deposited with the American Type Culture Collection (hereinafter referred to as "A.T.C.C."), 10801 University Blvd., Manassas, Va. 20110-2209, on Dec. 21, 2004 under the Budapest Treaty on the International Recognition of the Deposit of Microorganisms for the Purposes of Patent Procedure (Budapest Treaty of Apr. 28, 1977 and amended on Sep. 26, 1980, and assigned A.T.C.C. Accession No. PTA-6476.

One skilled in the art would readily appreciate that the present invention is well adapted to carry out the objects and obtain the ends and advantages mentioned, as well as those inherent therein. The molecular complexes and the methods, procedures, treatments, molecules, specific compounds described herein are presently representative of preferred embodiments, are exemplary, and are not intended as limitations on the scope of the invention. It will be readily apparent to one skilled in the art that varying substitutions and modifications may be made to the invention disclosed herein without departing from the scope and spirit of the invention.

All patents and publications mentioned in the specification are indicative of the levels of those skilled in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations which is not specifically disclosed herein. Thus, for example, in each instance herein any of the terms "comprising," "consisting essentially of" and "consisting of" may be replaced with either of the other two terms. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

In addition, where features or aspects of the invention are described in terms of Markush groups, those skilled in the art will recognize that the invention is also thereby described in terms of any individual member or subgroup of members of the Markush group. For example, if X is described as selected from the group consisting of bromine, chlorine, and iodine, claims for X being bromine and claims for X being bromine and chlorine are fully described.

What is claimed is:

1. Hybridoma cell line 3-631-436 having A.T.C.C. Accession No. PTA-6476.

2. A monoclonal antibody or a BNP-antigen binding fragment thereof produced by hybridoma cell line 3-631-436, wherein said cell line has A.T.C.C. Accession No. PTA-6476.

\* \* \* \* \*

UNITED STATES PATENT AND TRADEMARK OFFICE
CERTIFICATE OF CORRECTION

PATENT NO. : 7,731,965 B2  
APPLICATION NO. : 11/135040  
DATED : June 8, 2010  
INVENTOR(S) : Shih et al.

Page 1 of 1

It is certified that error appears in the above-identified patent and that said Letters Patent is hereby corrected as shown below:

On the title page of the patent, Item (73) should read:

--(73)   Assignee:  Abbott Laboratories, Abbott Park, IL--

Signed and Sealed this  
Fifth Day of March, 2013

Teresa Stanek Rea  
*Acting Director of the United States Patent and Trademark Office*

SEQUENCE LISTING

<160> NUMBER OF SEQ ID NOS: 36

<210> SEQ ID NO 1
<211> LENGTH: 32
<212> TYPE: PRT
<213> ORGANISM: Artificial Sequence
<220> FEATURE:
<223> OTHER INFORMATION: Cyclized hBNP

<400> SEQUENCE: 1

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Leu Arg Arg His
            20                  25                  30

<210> SEQ ID NO 2
<211> LENGTH: 26
<212> TYPE: PRT
<213> ORGANISM: Artificial Sequence
<220> FEATURE:
<223> OTHER INFORMATION: Modified cyclic BNP

<400> SEQUENCE: 2

Ser Pro Lys Met Val Gln Gly Ser Gly Cys Phe Gly Arg Lys Met Asp
 1               5                  10                  15

Arg Ile Ser Ser Ser Ser Gly Leu Gly Cys
            20                  25

<210> SEQ ID NO 3
<211> LENGTH: 26
<212> TYPE: PRT
<213> ORGANISM: Artificial Sequence
<220> FEATURE:
<223> OTHER INFORMATION: Biotinylated, modified cyclic BNP

<400> SEQUENCE: 3

Ser Pro Lys Met Val Gln Gly Ser Gly Cys Phe Gly Arg Lys Met Asp
 1               5                  10                  15

Arg Ile Ser Ser Ser Ser Gly Leu Gly Cys
            20                  25

<210> SEQ ID NO 4
<211> LENGTH: 17
<212> TYPE: PRT
<213> ORGANISM: Artificial Sequence
<220> FEATURE:
<223> OTHER INFORMATION: Modified cyclic BNP

<400> SEQUENCE: 4

Cys Phe Gly Arg Lys Met Asp Arg Ile Ser Ser Ser Ser Gly Leu Gly
 1               5                  10                  15

Cys

<210> SEQ ID NO 5
<211> LENGTH: 32
<212> TYPE: PRT
<213> ORGANISM: Artificial Sequence
<220> FEATURE:
<223> OTHER INFORMATION: Biotinylated cyclic BNP

<400> SEQUENCE: 5

Ser Pro Lys Met Val Gln Gly Ser Gly Cys Phe Gly Arg Lys Met Asp
 1               5                  10                  15

```
Arg Ile Ser Ser Ser Ser Gly Leu Gly Cys Lys Val Leu Arg Arg His
            20                  25                  30

<210> SEQ ID NO 6
<211> LENGTH: 6
<212> TYPE: PRT
<213> ORGANISM: Artificial Sequence
<220> FEATURE:
<223> OTHER INFORMATION: C-terminus of  cyclic BNP

<400> SEQUENCE: 6

Lys Val Leu Arg Arg His
1               5

<210> SEQ ID NO 7
<211> LENGTH: 28
<212> TYPE: PRT
<213> ORGANISM: Artificial Sequence
<220> FEATURE:
<223> OTHER INFORMATION: Cyclic ANP-28

<400> SEQUENCE: 7

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 8
<211> LENGTH: 22
<212> TYPE: PRT
<213> ORGANISM: Artificial Sequence
<220> FEATURE:
<223> OTHER INFORMATION: Cyclic CNP-22

<400> SEQUENCE: 8

Gly Leu Ser Lys Gly Cys Phe Gly Leu Lys Leu Asp Arg Ile Gly Ser
1               5                   10                  15

Met Ser Gly Leu Gly Cys
            20

<210> SEQ ID NO 9
<211> LENGTH: 32
<212> TYPE: PRT
<213> ORGANISM: Artificial Sequence
<220> FEATURE:
<223> OTHER INFORMATION: BNP S1A

<400> SEQUENCE: 9

Ala Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 10
<211> LENGTH: 32
<212> TYPE: PRT
<213> ORGANISM: Artificial Sequence
<220> FEATURE:
<223> OTHER INFORMATION: BNP P2A

<400> SEQUENCE: 10

Ser Ala Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
```

20                  25                  30

<210> SEQ ID NO 11
<211> LENGTH: 32
<212> TYPE: PRT
<213> ORGANISM: Artificial Sequence
<220> FEATURE:
<223> OTHER INFORMATION: BNP K3A

<400> SEQUENCE: 11

Ser Pro Ala Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 12
<211> LENGTH: 32
<212> TYPE: PRT
<213> ORGANISM: Artificial Sequence
<220> FEATURE:
<223> OTHER INFORMATION: BNP M4A

<400> SEQUENCE: 12

Ser Pro Lys Ala Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 13
<211> LENGTH: 32
<212> TYPE: PRT
<213> ORGANISM: Artificial Sequence
<220> FEATURE:
<223> OTHER INFORMATION: BNP V5A

<400> SEQUENCE: 13

Ser Pro Lys Met Ala Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 14
<211> LENGTH: 32
<212> TYPE: PRT
<213> ORGANISM: Artificial Sequence
<220> FEATURE:
<223> OTHER INFORMATION: BNP Q6A

<400> SEQUENCE: 14

Ser Pro Lys Met Val Ala Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 15
<211> LENGTH: 32
<212> TYPE: PRT
<213> ORGANISM: Artificial Sequence
<220> FEATURE:
<223> OTHER INFORMATION: BNP G7A

<400> SEQUENCE: 15

Ser Pro Lys Met Val Gln Ala Ser Gly Cys Phe Gly Arg Lys Met Asp
1               5                   10                  15

```
Arg Ile Ser Ser Ser Ser Gly Leu Gly Cys Lys Val Leu Arg Arg His
            20                  25                  30

<210> SEQ ID NO 16
<211> LENGTH: 32
<212> TYPE: PRT
<213> ORGANISM: Artificial Sequence
<220> FEATURE:
<223> OTHER INFORMATION: BNP S8A

<400> SEQUENCE: 16

Ser Pro Lys Met Val Gln Gly Ala Gly Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 17
<211> LENGTH: 32
<212> TYPE: PRT
<213> ORGANISM: Artificial Sequence
<220> FEATURE:
<223> OTHER INFORMATION: BNP G9A

<400> SEQUENCE: 17

Ser Pro Lys Met Val Gln Gly Ser Ala Cys Phe Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 18
<211> LENGTH: 32
<212> TYPE: PRT
<213> ORGANISM: Artificial Sequence
<220> FEATURE:
<223> OTHER INFORMATION: BNP F11A

<400> SEQUENCE: 18

Ser Pro Lys Met Val Gln Gly Ser Gly Cys Ala Gly Arg Lys Met Asp
1               5                   10                  15

Arg Ile Ser Ser Ser Ser Gly Leu Gly Cys Lys Val Leu Arg Arg His
            20                  25                  30

<210> SEQ ID NO 19
<211> LENGTH: 32
<212> TYPE: PRT
<213> ORGANISM: Artificial Sequence
<220> FEATURE:
<223> OTHER INFORMATION: BNP G12A

<400> SEQUENCE: 19

Ser Pro Lys Met Val Gln Gly Ser Gly Cys Phe Ala Arg Lys Met Asp
1               5                   10                  15

Arg Ile Ser Ser Ser Ser Gly Leu Gly Cys Lys Val Leu Arg Arg His
            20                  25                  30

<210> SEQ ID NO 20
<211> LENGTH: 32
<212> TYPE: PRT
<213> ORGANISM: Artificial Sequence
<220> FEATURE:
<223> OTHER INFORMATION: BNP R13A

<400> SEQUENCE: 20

Ser Pro Lys Met Val Gln Gly Ser Gly Cys Phe Gly Ala Lys Met Asp
1               5                   10                  15
```

Arg Ile Ser Ser Ser Ser Gly Leu Gly Cys Lys Val Leu Arg Arg His
            20                  25                  30

<210> SEQ ID NO 21
<211> LENGTH: 32
<212> TYPE: PRT
<213> ORGANISM: Artificial Sequence
<220> FEATURE:
<223> OTHER INFORMATION: BNP K14A

<400> SEQUENCE: 21

Ser Pro Lys Met Val Gln Gly Ser Gly Cys Phe Gly Arg Ala Met Asp
1               5                   10                  15

Arg Ile Ser Ser Ser Ser Gly Leu Gly Cys Lys Val Leu Arg Arg His
            20                  25                  30

<210> SEQ ID NO 22
<211> LENGTH: 32
<212> TYPE: PRT
<213> ORGANISM: Artificial Sequence
<220> FEATURE:
<223> OTHER INFORMATION: BNP M15A

<400> SEQUENCE: 22

Ser Pro Lys Met Val Gln Gly Ser Gly Cys Phe Gly Arg Lys Ala Asp
1               5                   10                  15

Arg Ile Ser Ser Ser Ser Gly Leu Gly Cys Lys Val Leu Arg Arg His
            20                  25                  30

<210> SEQ ID NO 23
<211> LENGTH: 32
<212> TYPE: PRT
<213> ORGANISM: Artificial Sequence
<220> FEATURE:
<223> OTHER INFORMATION: BNP D16A

<400> SEQUENCE: 23

Ser Pro Lys Met Val Gln Gly Ser Gly Cys Phe Gly Arg Lys Met Ala
1               5                   10                  15

Arg Ile Ser Ser Ser Ser Gly Leu Gly Cys Lys Val Leu Arg Arg His
            20                  25                  30

<210> SEQ ID NO 24
<211> LENGTH: 32
<212> TYPE: PRT
<213> ORGANISM: Artificial Sequence
<220> FEATURE:
<223> OTHER INFORMATION: BNP R17A

<400> SEQUENCE: 24

Ser Pro Lys Met Val Gln Gly Ser Gly Cys Phe Gly Arg Lys Met Asp
1               5                   10                  15

Ala Ile Ser Ser Ser Ser Gly Leu Gly Cys Lys Val Leu Arg Arg His
            20                  25                  30

<210> SEQ ID NO 25
<211> LENGTH: 32
<212> TYPE: PRT
<213> ORGANISM: Artificial Sequence
<220> FEATURE:
<223> OTHER INFORMATION: BNP I18A

<400> SEQUENCE: 25

Ser Pro Lys Met Val Gln Gly Ser Gly Cys Phe Gly Arg Lys Met Asp

```
                1               5              10              15
Arg Ala Ser Ser Ser Gly Leu Gly Cys Lys Val Leu Arg Arg His
                20              25              30

<210> SEQ ID NO 26
<211> LENGTH: 32
<212> TYPE: PRT
<213> ORGANISM: Artificial Sequence
<220> FEATURE:
<223> OTHER INFORMATION: BNP S19A

<400> SEQUENCE: 26

Ser Pro Lys Met Val Gln Gly Ser Gly Cys Phe Gly Arg Lys Met Asp
  1               5              10              15

Arg Ile Ala Ser Ser Gly Leu Gly Cys Lys Val Leu Arg Arg His
                20              25              30

<210> SEQ ID NO 27
<211> LENGTH: 32
<212> TYPE: PRT
<213> ORGANISM: Artificial Sequence
<220> FEATURE:
<223> OTHER INFORMATION: BNP S20A

<400> SEQUENCE: 27

Ser Pro Lys Met Val Gln Gly Ser Gly Cys Phe Gly Arg Lys Met Asp
  1               5              10              15

Arg Ile Ser Ala Ser Gly Leu Gly Cys Lys Val Leu Arg Arg His
                20              25              30

<210> SEQ ID NO 28
<211> LENGTH: 32
<212> TYPE: PRT
<213> ORGANISM: Artificial Sequence
<220> FEATURE:
<223> OTHER INFORMATION: BNP S21A

<400> SEQUENCE: 28

Ser Pro Lys Met Val Gln Gly Ser Gly Cys Phe Gly Arg Lys Met Asp
  1               5              10              15

Arg Ile Ser Ser Ala Ser Gly Leu Gly Cys Lys Val Leu Arg Arg His
                20              25              30

<210> SEQ ID NO 29
<211> LENGTH: 32
<212> TYPE: PRT
<213> ORGANISM: Artificial Sequence
<220> FEATURE:
<223> OTHER INFORMATION: BNP S22A

<400> SEQUENCE: 29

Ser Pro Lys Met Val Gln Gly Ser Gly Cys Phe Gly Arg Lys Met Asp
  1               5              10              15

Arg Ile Ser Ser Ser Ala Gly Leu Gly Cys Lys Val Leu Arg Arg His
                20              25              30

<210> SEQ ID NO 30
<211> LENGTH: 32
<212> TYPE: PRT
<213> ORGANISM: Artificial Sequence
<220> FEATURE:
<223> OTHER INFORMATION: BNP G23A

<400> SEQUENCE: 30
```

-continued

Ser Pro Lys Met Val Gln Gly Ser Gly Cys Phe Gly Arg Lys Met Asp
1               5                   10                  15

Arg Ile Ser Ser Ser Ala Leu Gly Cys Lys Val Leu Arg Arg His
        20                  25                  30

<210> SEQ ID NO 31
<211> LENGTH: 32
<212> TYPE: PRT
<213> ORGANISM: Artificial Sequence
<220> FEATURE:
<223> OTHER INFORMATION: BNP L24A

<400> SEQUENCE: 31

Ser Pro Lys Met Val Gln Gly Ser Gly Cys Phe Gly Arg Lys Met Asp
1               5                   10                  15

Arg Ile Ser Ser Ser Ser Gly Ala Gly Cys Lys Val Leu Arg Arg His
        20                  25                  30

<210> SEQ ID NO 32
<211> LENGTH: 32
<212> TYPE: PRT
<213> ORGANISM: Artificial Sequence
<220> FEATURE:
<223> OTHER INFORMATION: BNP K27A

<400> SEQUENCE: 32

Ser Pro Lys Met Val Gln Gly Ser Gly Cys Phe Gly Arg Lys Met Asp
1               5                   10                  15

Arg Ile Ser Ser Ser Ser Gly Leu Gly Cys Ala Val Leu Arg Arg His
        20                  25                  30

<210> SEQ ID NO 33
<211> LENGTH: 32
<212> TYPE: PRT
<213> ORGANISM: Artificial Sequence
<220> FEATURE:
<223> OTHER INFORMATION: BNP V28A

<400> SEQUENCE: 33

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Ala Leu Arg Arg His
        20                  25                  30

<210> SEQ ID NO 34
<211> LENGTH: 32
<212> TYPE: PRT
<213> ORGANISM: Artificial Sequence
<220> FEATURE:
<223> OTHER INFORMATION: BNP R30A

<400> SEQUENCE: 34

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Ala Arg His
        20                  25                  30

<210> SEQ ID NO 35
<211> LENGTH: 32
<212> TYPE: PRT
<213> ORGANISM: Artificial Sequence
<220> FEATURE:
<223> OTHER INFORMATION: BNP R31A

<400> SEQUENCE: 35

```
Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Leu Arg Ala His
                20                  25                  30

<210> SEQ ID NO 36
<211> LENGTH: 32
<212> TYPE: PRT
<213> ORGANISM: Artificial Sequence
<220> FEATURE:
<223> OTHER INFORMATION: BNP H32A

<400> SEQUENCE: 36

Ser Pro Lys Met Val Gln Gly Ser Gly Cys Phe Gly Arg Lys Met Asp
 1               5                  10                  15

Arg Ile Ser Ser Ser Ser Gly Leu Gly Cys Lys Val Leu Arg Arg Ala
                20                  25                  30
```